United States Patent
Hancock et al.

(10) Patent No.: US 6,818,407 B2
(45) Date of Patent: Nov. 16, 2004

(54) ANTI-ENDOTOXIC ANTIMICROBIAL CATIONIC PEPTIDES AND METHODS OF USE THERFOR

(75) Inventors: Robert E. W. Hancock, Vancouver (CA); Monisha A. Gough, Vancouver (CA); Aleksander Patrzykat, Vancouver (CA); Donald Woods, Calgary (CA); Xiaoyan Jia, New Westminster (CA)

(73) Assignee: The University of British Columbia, Vancouver (CA)

( * ) Notice: Subject to any disclaimer, the term of this patent is extended or adjusted under 35 U.S.C. 154(b) by 526 days.

(21) Appl. No.: 09/908,139

(22) Filed: Jul. 17, 2001

(65) Prior Publication Data

US 2003/0096949 A1 May 22, 2003

Related U.S. Application Data

(62) Division of application No. 09/143,124, filed on Aug. 28, 1998, now Pat. No. 6,288,212.

(51) Int. Cl.[7] .............................................. G01N 33/53
(52) U.S. Cl. ................... 435/7.1; 435/7.1; 435/235.1; 435/325; 530/350; 530/300; 530/324; 514/2; 514/12; 514/21
(58) Field of Search ...................... 435/7.1, 325, 235.1; 530/350, 300, 324; 514/2, 12, 21

(56) References Cited

FOREIGN PATENT DOCUMENTS

WO   WO 89/00199    1/1989
WO   WO 96/38473    * 12/1996

OTHER PUBLICATIONS

R.J. Wall, *Transgenic Livestock: Progress and Prospects for the Future*, Theriogenology, 45:57–68 (1996).

Gabay et al., "Antibiotic proteins of human polymorphonuclear leukocytes," *Proc. Natl. Acad. Sci. USA*, 86:5610–5614 (1989).

Romeo et al., "Structure and Bacterial Activity of an Antibiotic Dodecapeptide Purified from Bovine Neutrophils," *The Journal of Biological Chemistry*, 263(20):9573–9575.

Zasloff et al., "Antimicrobial activity of synthetic magainin peptides and several analogues, " *Proc. Natl. Acad. Sci. USA*, 85:910–913 (1988).

* cited by examiner

*Primary Examiner*—Robert A. Wax
*Assistant Examiner*—Hope A. Robinson
(74) *Attorney, Agent, or Firm*—Gray Cary Ware & Freidenrich, LLP

(57) ABSTRACT

A novel class of cationic peptides having antimicrobial activity is provided. Exemplary peptides of the invention include KWKSFIKKLTSAAKKVVTTAKPLALIS (SEQ ID NO:3) and KGWGSFFKKAAHVGKHVGKAALTHYL (SEQ ID NO:15). Also provided are methods for inhibiting the growth of bacteria utilizing the peptides of the invention. Such methods are useful for the treatment of respiratory infections, such as in cystic fibrosis patients. Such methods are further useful for accelerating wound healing.

21 Claims, 3 Drawing Sheets

ID

SEQUENCE LISTING

```
<160> NUMBER OF SEQ ID NOS: 25

<210> SEQ ID NO 1
<211> LENGTH: 28
<212> TYPE: PRT
<213> ORGANISM: Artificial Sequence
<220> FEATURE:
<223> OTHER INFORMATION: antimicrobial cationic peptide

<400> SEQUENCE: 1

Lys Trp Lys Leu Phe Lys Lys Ile Gly Ile Gly Ala Val Leu Lys Val
1               5                   10                  15

Leu Thr Thr Gly Leu Pro Ala Leu Lys Leu Thr Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: antimicrobial cationic peptide

<400> SEQUENCE: 2

Lys Trp Lys Ser Phe Ile Lys Lys Leu Thr Thr Ala Val Lys Lys Val
1               5                   10                  15

Leu Thr Thr Gly Leu Pro Ala Leu Ile Ser
            20                  25

<210> SEQ ID NO 3
<211> LENGTH: 27
<212> TYPE: PRT
<213> ORGANISM: Artificial Sequence
<220> FEATURE:
<223> OTHER INFORMATION: antimicrobial cationic peptide

<400> SEQUENCE: 3

Lys Trp Lys Ser Phe Ile Lys Lys Leu Thr Ser Ala Ala Lys Lys Val
1               5                   10                  15

Val Thr Thr Ala Lys Pro Leu Ala Leu Ile Ser
            20                  25

<210> SEQ ID NO 4
<211> LENGTH: 26
```

<212> TYPE: PRT
<213> ORGANISM: Artificial Sequence
<220> FEATURE:
<223> OTHER INFORMATION: antimicrobial cationic peptide

<400> SEQUENCE: 4

Lys Trp Lys Ser Phe Ile Lys Lys Leu Thr Lys Ala Ala Lys Val
1               5                   10                  15

Val Thr Thr Ala Lys Lys Pro Leu Ile Val
            20                  25

<210> SEQ ID NO 5
<211> LENGTH: 27
<212> TYPE: PRT
<213> ORGANISM: Artificial Sequence
<220> FEATURE:
<223> OTHER INFORMATION: antimicrobial cationic peptide

<400> SEQUENCE: 5

Lys Trp Lys Lys Phe Ile Lys Ser Leu Thr Lys Ser Ala Ala Lys Thr
1               5                   10                  15

Val Val Lys Thr Ala Lys Lys Pro Leu Ile Val
            20                  25

<210> SEQ ID NO 6
<211> LENGTH: 32
<212> TYPE: PRT
<213> ORGANISM: Artificial Sequence
<220> FEATURE:
<223> OTHER INFORMATION: antimicrobial cationic peptide

<400> SEQUENCE: 6

Lys Trp Lys Leu Phe Lys Lys Ile Gly Ile Gly Ala Val Leu Lys Val
1               5                   10                  15

Leu Lys Val Leu Thr Thr Gly Leu Pro Ala Leu Lys Leu Thr Leu Lys
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: antimicrobial cationic peptide

<400> SEQUENCE: 7

Lys Leu Phe Lys Lys Ile Gly Ile Gly Ala Val Leu Lys Val Leu Lys
1               5                   10                  15

Val Leu Thr Thr Gly Leu Pro Ala Leu Lys Leu Thr Leu Lys
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: antimicrobial cationic peptide

<400> SEQUENCE: 8

Lys Trp Lys Phe Lys Lys Ile Gly Ile Gly Ala Val Leu Lys Val Leu
1               5                   10                  15

Lys Val Leu Thr Thr Gly Leu Pro Ala Leu Lys Leu Thr Leu Lys
            20                  25                  30

<210> SEQ ID NO 9

```
<211> LENGTH: 33
<212> TYPE: PRT
<213> ORGANISM: Artificial Sequence
<220> FEATURE:
<223> OTHER INFORMATION: antimicrobial cationic peptide

<400> SEQUENCE: 9

Lys Leu Trp Lys Leu Phe Lys Lys Ile Gly Ile Gly Ala Val Leu Lys
 1               5                  10                  15

Val Leu Lys Val Leu Thr Thr Gly Leu Pro Ala Leu Lys Leu Thr Leu
            20                  25                  30
Lys

<210> SEQ ID NO 10
<211> LENGTH: 25
<212> TYPE: PRT
<213> ORGANISM: Artificial Sequence
<220> FEATURE:
<223> OTHER INFORMATION: antimicrobial cationic peptide

<400> SEQUENCE: 10

Lys Trp Lys Ser Phe Ile Lys Lys Leu Thr Ser Ala Ala Lys Lys Val
 1               5                  10                  15

Thr Thr Ala Ala Lys Pro Leu Thr Lys
            20                  25

<210> SEQ ID NO 11
<211> LENGTH: 30
<212> TYPE: PRT
<213> ORGANISM: Artificial Sequence
<220> FEATURE:
<223> OTHER INFORMATION: antimicrobial cationic peptide

<400> SEQUENCE: 11

Lys Trp Lys Lys Phe Ile Lys Lys Ile Gly Ile Gly Ala Val Leu Lys
 1               5                  10                  15

Val Leu Thr Thr Gly Leu Pro Ala Leu Lys Leu Thr Lys Lys
            20                  25                  30

<210> SEQ ID NO 12
<211> LENGTH: 23
<212> TYPE: PRT
<213> ORGANISM: Artificial Sequence
<220> FEATURE:
<223> OTHER INFORMATION: antimicrobial cationic peptide

<400> SEQUENCE: 12

Lys Lys Trp Lys Lys Phe Ile Lys Lys Ile Gly Ile Gly Ala Val Leu
 1               5                  10                  15

Thr Thr Pro Gly Ala Lys Lys
            20

<210> SEQ ID NO 13
<211> LENGTH: 25
<212> TYPE: PRT
<213> ORGANISM: Artificial Sequence
<220> FEATURE:
<223> OTHER INFORMATION: antimicrobial cationic peptide

<400> SEQUENCE: 13

Gly Trp Gly Ser Phe Phe Lys Lys Ala Ala His Val Gly Lys His Val
 1               5                  10                  15

Gly Lys Ala Ala Leu Thr His Tyr Leu
            20                  25
```

```
<210> SEQ ID NO 14
<211> LENGTH: 25
<212> TYPE: PRT
<213> ORGANISM: Artificial Sequence
<220> FEATURE:
<223> OTHER INFORMATION: antimicrobial cationic peptide
<221> NAME/KEY: AMIDATION
<222> LOCATION: (0)...(0)
<223> OTHER INFORMATION: amidated leucine (Leu) at C-terminus

<400> SEQUENCE: 14

Gly Trp Gly Ser Phe Phe Lys Lys Ala Ala His Val Gly Lys His Val
 1               5                  10                  15

Gly Lys Ala Ala Leu Thr His Tyr Leu
            20                  25

<210> SEQ ID NO 15
<211> LENGTH: 26
<212> TYPE: PRT
<213> ORGANISM: Artificial Sequence
<220> FEATURE:
<223> OTHER INFORMATION: antimicrobial cationic peptide

<400> SEQUENCE: 15

Lys Gly Trp Gly Ser Phe Phe Lys Lys Ala Ala His Val Gly Lys His
 1               5                  10                  15

Val Gly Lys Ala Ala Leu Thr His Tyr Leu
            20                  25

<210> SEQ ID NO 16
<211> LENGTH: 26
<212> TYPE: PRT
<213> ORGANISM: Artificial Sequence
<220> FEATURE:
<223> OTHER INFORMATION: antimicrobial cationic peptide
<221> NAME/KEY: AMIDATION
<222> LOCATION: (0)...(0)
<223> OTHER INFORMATION: amidated leucine (Leu) at C-terminus

<400> SEQUENCE: 16

Lys Gly Trp Gly Ser Phe Phe Lys Lys Ala Ala His Val Gly Lys His
 1               5                  10                  15

Val Gly Lys Ala Ala Leu Thr His Tyr Leu
            20                  25

<210> SEQ ID NO 17
<211> LENGTH: 26
<212> TYPE: PRT
<213> ORGANISM: Artificial Sequence
<220> FEATURE:
<223> OTHER INFORMATION: antimicrobial cationic peptide
<221> NAME/KEY: AMIDATION
<222> LOCATION: (0)...(0)
<223> OTHER INFORMATION: amidated leucine (Leu) at C-terminus

<400> SEQUENCE: 17

Ala Leu Trp Lys Thr Met Leu Lys Lys Ala Ala His Val Gly Lys His
 1               5                  10                  15

Val Gly Lys Ala Ala Leu Thr His Tyr Leu
            20                  25

<210> SEQ ID NO 18
<211> LENGTH: 25
<212> TYPE: PRT
<213> ORGANISM: Artificial Sequence
<220> FEATURE:
```

```
<223> OTHER INFORMATION: antimicrobial cationic peptide
<221> NAME/KEY: AMIDATION
<222> LOCATION: (0)...(0)
<223> OTHER INFORMATION: amidated leucine (Leu) at C-terminus

<400> SEQUENCE: 18

Ser Ile Gly Ser Ala Phe Lys Lys Ala Ala His Val Gly Lys His Val
 1               5                  10                  15

Gly Lys Ala Ala Leu Thr His Tyr Leu
            20                  25

<210> SEQ ID NO 19
<211> LENGTH: 29
<212> TYPE: PRT
<213> ORGANISM: Artificial Sequence
<220> FEATURE:
<223> OTHER INFORMATION: antimicrobial cationic peptide

<400> SEQUENCE: 19

Gly Trp Gly Ser Phe Phe Lys Lys Ala Ala His Val Gly Lys His Val
 1               5                  10                  15

Gly Lys Ala Ala Leu Gly Ala Ala Ala Arg Arg Arg Lys
            20                  25

<210> SEQ ID NO 20
<211> LENGTH: 30
<212> TYPE: PRT
<213> ORGANISM: Artificial Sequence
<220> FEATURE:
<223> OTHER INFORMATION: antimicrobial cationic peptide

<400> SEQUENCE: 20

Ala Leu Trp Lys Thr Met Leu Lys Lys Ala Ala His Val Gly Lys His
 1               5                  10                  15

Val Gly Lys Ala Ala Leu Gly Ala Ala Ala Arg Arg Arg Lys
            20                  25                  30

<210> SEQ ID NO 21
<211> LENGTH: 29
<212> TYPE: PRT
<213> ORGANISM: Artificial Sequence
<220> FEATURE:
<223> OTHER INFORMATION: antimicrobial cationic peptide

<400> SEQUENCE: 21

Ser Ile Gly Ser Ala Phe Lys Lys Ala Ala His Val Gly Lys His Val
 1               5                  10                  15

Gly Lys Ala Ala Leu Gly Ala Ala Ala Arg Arg Arg Lys
            20                  25

<210> SEQ ID NO 22
<211> LENGTH: 21
<212> TYPE: PRT
<213> ORGANISM: Artificial Sequence
<220> FEATURE:
<223> OTHER INFORMATION: antimicrobial cationic peptide

<400> SEQUENCE: 22

Arg Gln Arg Val Glu Glu Leu Ser Lys Phe Ser Lys Lys Gly Ala Ala
 1               5                  10                  15

Ala Arg Arg Arg Lys
            20

<210> SEQ ID NO 23
```

-continued

```
<211> LENGTH: 33
<212> TYPE: PRT
<213> ORGANISM: Artificial Sequence
<220> FEATURE:
<223> OTHER INFORMATION: antimicrobial cationic peptide

<400> SEQUENCE: 23

Ala Leu Trp Lys Thr Met Leu Lys Lys Leu Gly Thr Met Ala Leu His
 1               5                  10                  15

Ala Gly Lys Ala Ala Leu Gly Ala Ala Ala Asp Thr Ile Ser Gln Thr
            20                  25                  30
Gln

<210> SEQ ID NO 24
<211> LENGTH: 29
<212> TYPE: PRT
<213> ORGANISM: Artificial Sequence
<220> FEATURE:
<223> OTHER INFORMATION: antimicrobial cationic peptide

<400> SEQUENCE: 24

Ser Ile Gly Ser Ala Phe Lys Lys Ala Leu Pro Val Ala Lys Lys Ile
 1               5                  10                  15

Gly Lys Ala Ala Leu Pro Ile Ala Lys Ala Ala Leu Pro
            20                  25

<210> SEQ ID NO 25
<211> LENGTH: 26
<212> TYPE: PRT
<213> ORGANISM: Artificial Sequence
<220> FEATURE:
<223> OTHER INFORMATION: antimicrobial cationic peptide

<400> SEQUENCE: 25

Lys Trp Lys Ser Phe Ile Lys Lys Leu Thr Ser Ala Ala Lys Lys Val
 1               5                  10                  15

Val Thr Thr Ala Lys Pro Leu Ile Ser Ser
            20                  25
```

ANTI-ENDOTOXIC ANTIMICROBIAL CATIONIC PEPTIDES AND METHODS OF USE THERFOR

This application is a divisional of U.S. application Ser. No. 09/143,124, filed Aug. 28, 1998 now U.S. Pat. No. 6,288,212 and is incorporated by reference.

BACKGROUND OF THE INVENTION

1. Field of the Invention

This invention relates generally to antimicrobial peptides and specifically to antimicrobial cationic peptides useful for overcoming antibiotic resistance and effective as therapeutics for pathologies resulting from microbial infections.

2. Description of Related Art

In 1981, the self-promoted uptake hypothesis was first proposed to explain the mechanism of action of polycationic antibiotics in *Pseudomonas aeruginosa*. According to this hypothesis, polycations interact with sites on the outer membranes of Gram-negative bacteria at which divalent cations cross-bridge adjacent lipopolysaccharide molecules. Due to their higher affinity for these sites, polycations displace the divalent cations and, since the polycations are bulkier than the divalent cations, cause structural perturbations in the outer membrane. These perturbations result in increased outer membrane permeability to compounds such as the β-lactam antibiotic nitrocefin, the eukaryotic non-specific defense protein lysozyme and to hydrophobic substances. By analogy, molecules accessing this pathway are proposed to promote their own uptake.

It has been clearly demonstrated that the outer membranes of Gram-negative bacteria are semipermeable molecular Asieves≈ which restrict access of antibiotics and host defense molecules to their targets within the bacterial cell. Thus, cations and polycations which access the self-promoted uptake system are, by virtue of their ability to interact with and break down the outer membrane permeability barrier, capable of increasing the susceptibility of Gram-negative pathogenic bacteria to antibiotics and host defense molecules. Hancock and Wong demonstrated that a broad range of such compounds could overcome the permeability barrier and coined the name Apermeabilizers≈ to describe them (Hancock and Wong, *Antimicrob. Agents Chemother.*, 26:48, 1984). While self-promoted uptake and permeabilizers were first described for *P. aeruginosa*, they have now been described for a variety of Gram-negative bacteria.

Over the past decade, non-specific defense molecules have been described in many animals, including insects and humans. One subset of these molecules have in common the following features: (a) they are small peptides, usually 15–35 amino acids in length, (b) they contain 4 or more positively charged amino acid residues, either lysines or arginines, and (c) they are found in high abundance in the organisms from which they derive. Several of these molecules have been isolated, amino acid sequenced and described in the patent literature (e.g., cecropins: WO8900199, WO 8805826, WO8604356, WO 8805826; defensins: EP 193351, EP 85250, EP 162161, U.S. Pat. No. 4,659,692, WO 8911291). However, only limited amounts of these peptides can be isolated from the host species. For example, Sawyer, et al., (*Infect. Immun.* 56:693, 1988) isolated 100–200 mg of rabbit neutrophil defensins 1 and 2 from $10^9$ primed peritoneal neutrophils or lipopolysaccharide-elicited alveolar macrophages (i.e., the numbers present in a whole animal).

Some cationic antibacterial peptides are of relatively high molecular weight (greater than about 25 kDa) and are effective against certain Gram negative bacteria such as *Escherichia coli*, *Salmonella typhimurium* and *Pseudomonas aeruginosa* by damaging the cytoplasmic membrane leading to increased membrane permeability. Human bactericidal/permeability increasing protein (BPI) is a strongly basic protein with a molecular weight of about 59 kDa. It is believed that, when bound to outer membrane of the susceptible bacterial cells, hydrophobic channels through the outer envelope are exposed, and as a secondary effect, there is a selective activation of autolytic enzymes including phospholipase and peptidoglycan hydrolases. Gram positive bacteria, certain Gram negative bacteria and fungi are not affected by BPI in vitro.

Low molecular weight cationic peptides (10 kDa to 25 kDa) have been reported which inhibit the growth of such Gram positive bacteria as *Staphylococcus aureus* (Root and Cohen, *Rev. Infect. Dis.*, 3:565–598, 1981). In addition cationic peptides with fungicidal activity have been identified in alveolar macrophages. It is believed that cationic peptides are most efficient in killing phagocytized microorganisms in combination with other microbicidal defense mechanisms.

Generally defensins are relatively small polypeptides of about 3–4 kDa, rich in cysteine and arginine. Gabay et al. (*Proc. Natl. Acad. Sci. USA*, 86:5610–5614, 1989) used reversed phase HPLC to purify 12 major polypeptides from the azurophil granules of human polymorphonuclear leukocytes (PMNs). Defensins as a class have activity against some bacteria, fungi and viruses. The defensins are believed to have a molecular structure stabilized by cysteine infrastructure, which are essential for biological activity. The gene for human defensin has been cloned and sequenced, but no successful expression has been demonstrated, as yet. Furthermore, production of these peptides using peptide synthesis technology produces peptides in limited amounts and is expensive when scaled up or when many variant peptides must be produced. Also, structural analysis is difficult without specific incorporation of $^{15}N$ and $^{13}C$ tagged amino acids which is prohibitively expensive using amino acid synthesis technology.

Another class of antimicrobial peptides are those known as magainins and at least five of which can be isolated from the African clawed frog (*Xenopus laevis*). The natural proteins are active against a broad range of microorganisms including bacteria, fungi and protozoans (Zasloff, *Proc. Natl. Acad. Sci., USA*, 84:5499, 1987). The broad spectrum antimicrobial activity is present in synthetic peptides and in certain truncated analogs of the natural proteins. Derivatives of about 19 to about 23 amino acids have antibacterial activity as measured using *Escherichia coli*. In addition, the antimicrobial activity of magainin appears to result in the disruption of the membrane functions of *Paramecium caudatum*. The configurations of the bioactive peptides can be modeled as amphophilic alpha-helices and are sufficiently long to span a lipid bilayer (Zasloff et al., *Proc. Natl. Acad. Sci., USA*, 85:910, 1988). Spanning a lipid bilayer is believed to require at least twenty amino acid residues in an alpha-helical configuration (Kaiser, *Ann. Rev. Biophys. Chem.*, 16:562, 1987)

Cationic peptides containing a disulphide bond forming a looped structure were recently identified (Morikawa et al., *Biochim. Biophys. Res. Commun.* 189:184, 1992; Simmaco et al., FEBS 324:159, 1993; Clark et al., *J. Biol. Chem.* 269:10849, 1994). One member of this group, bactenecin (i.e., dodecapeptide), is a twelve amino acid peptide isolated from bovine neutrophils (Romeo et al., *J. Biol. Chem.* 263:9573, 1988). Bactenecin is the smallest known cationic antimicrobial peptide. Two cysteine residues form a disulphide bond to make bactenecin a loop molecule. Bactenecin was previously found to be active against *Escherischia coli* and *Staphylococcus aureus*, and strongly cytotoxic for rat embryonic neurons, fetal rat astrocytes and human glioblastoma cells (Radermacher et al., *J. Neuroscience Res.* 36:657, 1993).

Synthetic peptide chemistry has determined that α-helices are a common structural motif found in both antibacterial peptides that can act selectively on bacterial membranes (e.g., cecropin), and in cytotoxic peptides that can lyse both mammalian and bacterial cells (e.g., melittin). Cecropins were initially discovered in insects but later found in other animals including mammals. Electron microscopy has revealed that cecropin-induced inhibition of bacterial growth is due, in part, to bacterial wall lysis. Resistance to such a generally destructive mechanism may prove difficult for some microbial pathogens, as compared with the more specific mechanisms of the currently used antibiotics. Further, the bee venom peptide melittin is known to form channel-like structures in biological membranes and retrains pharmacological properties in intact tissues including hemolysis, cytolysis, contractures of muscle, membrane depolarization and activation of tissue phospholipase C.

There is a need to develop peptides having a broad range of potent antimicrobial activity against a plurality of microorganisms, including gram negative bacteria, gram positive bacteria, fungi, protozoa, parasites, viruses and the like. The identification of novel antimicrobial cationic peptides which overcome antibiotic resistance and are effective as therapeutics for microbial pathogens would aid in combating such organisms.

SUMMARY OF THE INVENTION

The present invention provides antimicrobial cationic peptides effective for inhibiting the growth of a plurality of microorganisms, including gram negative bacteria, gram positive bacteria, fungi, protozoa, parasites and viruses. Exemplary peptides include:

| | |
|---|---|
| NH$_2$-KWKSFIKKLTSAAKKVVTTAKPLALIS-COOH; | (SEQ ID NO:3) |
| KWKSFIKKLTKAAKKVVTTAKKPLIV; | (SEQ ID NO:4) |
| KWKKFIKSLTKSAAKTVVKTAKKPLIV; | (SEQ ID NO:5) |
| KWKLFKKIGIGAVLKVLKVLTTGLPALKLTLK; | (SEQ ID NO:6) |
| KLFKKIGIGAVLKVLKVLTTGLPALKLTLK; | (SEQ ID NO:7) |
| KWKFKKIGIGAVLKVLKVLTTGLPALKLTLK; | (SEQ ID NO:8) |
| KLWKLFKKIGIGAVLKVLKVLTTGLPALKLTLK; | (SEQ ID NO:9) |
| KWKSFIKKLTSAAKKVTTAAKPLTK; | (SEQ ID NO:10) |
| KWKKFIKKIGIGAVLKVLTTGLPALKLTKK; | (SEQ ID NO:11) |
| KKWKKFIKKIGIGAVLTTPGAKK; | (SEQ ID NO:12) |
| GWGSFFKKAAHVGKHVGKAALTHYL-NH2; | (SEQ ID NO:14) |
| KGWGSFFKKAAHVGKHVGKAALTHYL; | (SEQ ID NO:15) |
| KGWGSFFKKAAHVGKHVGKAALTHYL-NH2; | (SEQ ID NO:16) |
| ALWKTMLKKAAHVGKHVGKAALTHYL-NH2; | (SEQ ID NO:17) |
| SIGSAFKKAAHVGKHVGKAALTHYL-NH2; | (SEQ ID NO:18) |
| GWGSFFKKAAHVGKHVGKAALGAAARRRK; | (SEQ ID NO:19) |
| ALWKTMLKKAAHVGKHVGKAALGAAARRRK; | (SEQ ID NO:20) |
| SIGSAFKKAAHVGKHVGKAALGAAARRRK; | (SEQ ID NO:21) | and analogs, derivatives, amidated variations and conservative variations thereof.

The invention also provides a method of inhibiting the growth of bacteria including contacting the bacteria with an inhibiting effective amount of at least one peptide of the invention alone, or in combination with at least antibiotic. Classes of antibiotics that can be used in synergistic therapy with the peptides of the invention include aminoglycoside, penicillin, cephalosporine, fluoroquinolone, carbepenem, tetracycline and macrolides.

The invention further provides polynucleotides that encode the peptides of SEQ ID NOs:3–12 and 14–21 of the invention. In one aspect, amidated derivatives of antimicrobial peptides encoded by such polynucleotides are included in the invention.

In another embodiment, the invention provides a method of inhibiting an endotoxemia- or sepsis-associated disorder in a subject having or at risk of having such a disorder, by administering to the subject a therapeutically effective amount of at least one peptide of the invention.

The invention also provides a method of inhibiting the growth of a eukaryotic cell. The method includes contacting the cell with an inhibiting effective amount of a peptide or combination thereof of the invention, alone, or in combination with an agent effective for inhibiting eukaryotic cell growth. Such agents which can be used for synergistic therapy with the peptides of the invention include bleomycin, neocarcinostatin, suramin, doxorubicin, taxol, mitomycin C and cisplatin.

The invention further provides a method of inhibiting a cell proliferation-associated disorder in a subject having or at risk of having such a disorder. The method includes administering to the subject a therapeutically effective amount of at least one peptide of the invention, alone, or in combination with an agent effective for inhibiting eukaryotic cell growth. Such agents which can be used for synergistic therapy with the peptides of the invention include bleomycin, neocarcinostatin, suramin, doxorubicin, taxol, mitomycin C and cisplatin.

The invention further provides a method for accelerating wound healing in a subject in need of such treatment including contacting the site of the wound with a therapeutically effective amount of a composition containing an antimicrobial cationic peptide of the invention.

In another embodiment, the invention provides a method of treating a respiratory or pulmonary associated disorder in a subject having or at risk of having such a disorder, comprising administering to the subject a therapeutically effective amount of peptide.

In another embodiment, the invention provides a transgenic non-human animal expressing an antimicrobial cationic peptide of the invention.

In yet another embodiment the invention provides transgenic fish expressing an antimicrobial cationic peptide of the invention, a method for producing such a transgenic fish and a method for detecting expression of a transgene in a transgenic fish of the invention.

DETAILED DESCRIPTION OF THE INVENTION

Figure 1:
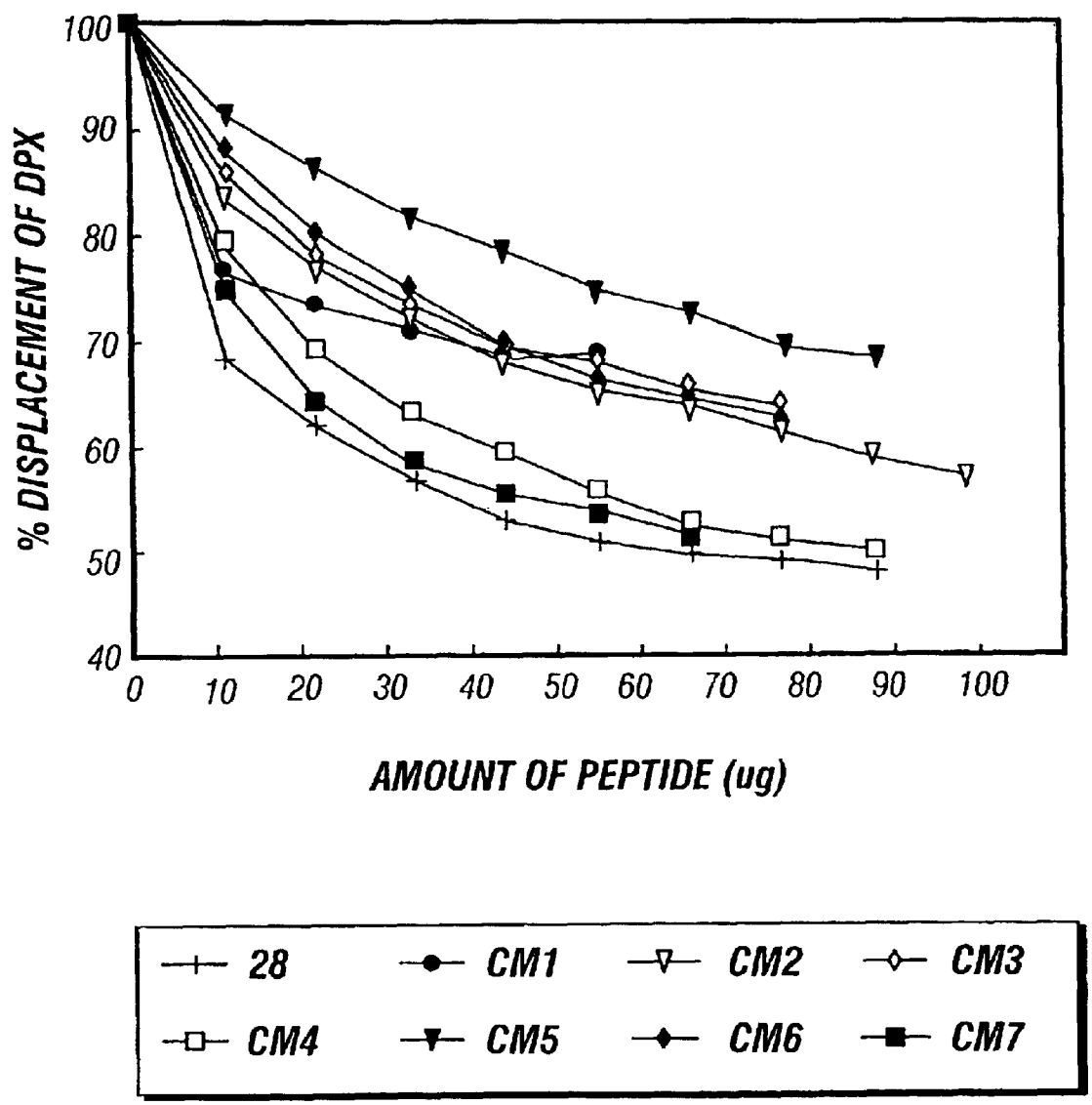
FIG. 1 is a graph which shows LPS (endotoxin) binding by the dansyl polymyxin binding assay. The anti-endotoxic activity of the peptides was tested in the murine cell line RAW 264.7 which was obtained from the ATCC (Rockville, Md.). Symbols in the graph are as follows: ΣΣ ΣΣ 28; ΣΣΜΣΣ CM1; ΣΣΣ↔ΣΣCM2; ΣΣ∀ ΣΣCM3; ΣΣΡΣΣ CM4; ΣΣ ΣΣ CM5; ΣΣ ΣΣCM6; ΣΣΠ ΣΣ CM7.

The present invention provides antimicrobial cationic peptides that have antimicrobial and anti-endotoxin activity. These peptides are useful for inhibiting microbial infection or growth, as well reducing the effects of endotoxemia. Many of the peptides also synergize with conventional antibiotics and/or lysozyme. In addition, such peptides are useful as antifungal agents, antitumor agents, or antiviral agents.

The term Aantimicrobial≅ as used herein means that the peptides of the present invention inhibit, prevent, or destroy the growth or proliferation of microbes such as bacteria, fungi, viruses, parasites or the like. The term Aantiviral≅ as used herein means that the peptides of the present invention inhibit, prevent or destroy the growth or proliferation of viruses or of virally-infected cells. The term Aanti-tumor≅ as used herein means that the peptides of the present invention may be used to inhibit the growth of tumor cells. The term Aantifungal≅ as used herein means that the peptides of the present invention may be used to inhibit the growth of or destroy fungi. The term Aantiparasite≅, as used herein, means that the peptides of the present invention inhibit, prevent, or destroy the growth or proliferation of any organism that lives at the expense of a host organism.

In a first embodiment, the invention provides isolated antimicrobial peptides. Exemplary peptides of the invention have an amino acid sequence including:

| | |
|---|---|
| NH<sub>2</sub>-KWKSFIKKLTSAAKKVVTTAKPLALIS-COOH; | (SEQ ID NO:3) |
| KWKSFIKKLTKAAKKVVTTAKKPLIV; | (SEQ ID NO:4) |
| KWKKIKSLTKSAAKTVVKTAKKPLIV; | (SEQ ID NO:5) |
| KWKLFKKIGIGAVLKVLKVLTTGLPALKLTLK; | (SEQ ID NO:6) |
| KLFKKIGIGAVLKVLKVLTTGLPALKLTLK; | (SEQ ID NO:7) |
| KWKFKKIGIGAVLKVLKVLTTGLPALKLTLK; | (SEQ ID NO:8) |
| KLWKLFKKIGIGAVLKVLKVLTTGLPALKLTLK; | (SEQ ID NO:9) |
| KWKSFIKKLTSAAKKVTTAAKPLTK; | (SEQ ID NO:10) |
| KWKKFIKKIGIGAVLKVLTTGLPALKTKK; | (SEQ ID NO:11) |
| KKWKKFIKKIGIGAVLTTPGAKK; | (SEQ ID NO:12) |
| GWGSFFKKAAHVGKHVGKAALTHYL-NH2; | (SEQ ID NO:14) |
| KGWGSFFKKAAHVGKHVGKAALTHYL; | (SEQ ID NO:15) |
| KGWGSFFKKAAHVGKHVGKAALTHYL-NH2; | (SEQ ID NO:16) |
| ALWKTMLKKAAHVGKHVGKAALTHYL-NH2; | (SEQ ID NO:17) |
| SIGSAFKKAAHVGKHVGKAALTHYL-NH2; | (SEQ ID NO:18) |
| GWGSFFKKAAHVGKHVGKAALGAAARRRK; | (SEQ ID NO:19) |
| ALWKTMLKKAAHVGKHVGKAALGAAARRRK; | (SEQ ID NO:20) |
| SIGSAFKKAAHVGKHVGKAALGAAARRRK; | (SEQ ID NO:21) | and analogs, derivatives, amidated variations and conservative variations thereof, wherein the peptides have antimicrobial activity. The peptides of the invention include SEQ ID NOS:3–12 and 14–21, as well as the broader groups of peptides having hydrophilic and hydrophobic substitutions, and conservative variations thereof.

The term Aisolated≅ as used herein refers to a peptide substantially free of proteins, lipids, nucleic acids, for example, with which it is naturally associated. Those of skill in the art can make similar substitutions to achieve peptides with greater antimicrobial activity and a broader host range. For example, the invention includes the peptides depicted in SEQ ID NOs:3–12 and 14–21, as well as analogues, derivatives and amidated derivatives thereof, as long as a bioactivity (e.g., antimicrobial) of the peptide remains. Minor modifications of the primary amino acid sequence of the peptides of the invention may result in peptides which have substantially equivalent or enhanced activity as compared to the specific peptides described herein. Such modifications may be deliberate, as by site-directed mutagenesis, or may be spontaneous. All of the peptides produced by these modifications are included herein as long as the biological activity of the original peptide still exists or, in the case of amidated versions of the peptide, the antimicrobial activity of the original peptide is enhanced or altered such that the amidated peptide is therapeutically useful. For example, the amino acid sequence of SEQ ID NO:16 is identical to that of SEQ ID NO:15. However, SEQ ID NO:16 is amidated at the C-terminal end thereby altering the animicrobial activity of the peptide. It is envisioned that such modifications are useful for altering or enhancing the biological activity of a particular peptide.

Further, deletion of one or more amino acids can also result in a modification of the structure of the resultant molecule without significantly altering its biological activity. This can led to the development of a smaller active molecule which would also have utility. For example, amino or carboxy terminal amino acids which may not be required for biological activity of the particular peptide can be removed. Peptides of the invention include any analog, homolog, mutant, isomer or derivative of the peptides disclosed in the present invention, so long as the bioactivity as described herein is remains. All peptides were synthesized using L amino acids, however, all D forms of the peptides (e.g., see Table 1 and Table 10) can be synthetically produced. In addition, C-terminal derivatives can be produced, such as C-terminal methyl esters and C-terminal amidates (e.g., see Table 1 and Table 10), in order to increase the antimicrobial activity of a peptide of the invention. The amino acid sequences of the peptides contained in Table 1 and Table 10 are recited in the N-terminal to C-terminal orientation. In addition, the notation A-NH2" on the C-terminal end of, for example, SEQ ID NOs:14 and 16–18 contained in Table 10, refers to an amidated modification of the C-terminus rather than designating the N-terminal end of the peptide.

A ≡peptide≡ of the invention includes amino acid sequences are conservative variations of those peptides specifically exemplified herein. The term ≡conservative variation≡ as used herein denotes the replacement of an amino acid residue by another, biologically similar residue. Examples of conservative variations include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. The term ≡conservative variation≡ also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention.

The biological activity of the peptides can be determined by standard methods known to those of skill in the art, such as ≡minimal inhibitory concentration (MIC)≡ assay described in the present examples, whereby the lowest concentration at which no change in OD is observed for a given period of time is recorded as MIC. Alternatively, ≡fractional inhibitory concentration (FIC)≡ is also useful for determination of synergy between the peptides of the invention, or the peptides in combination with known antibiotics. FICs are performed by checkerboard titrations of peptides in one dimension of a microtiter plate, and of antibiotics in the other dimension, for example. The FIC is calculated by looking at the impact of one antibiotic on the MIC of the other and vice versa. An FIC of one indicates that the influence of the compounds is additive and an FIC of less than one indicates synergy. Preferably, an FIC of less than 0.5 is obtained for synergism. As used herein, FIC can be determined as follows:

$$FIC = \frac{MIC \text{ (peptide in combination)}}{MIC \text{ (peptide alone)}} + \frac{MIC \text{ (antibiotic in combination)}}{MIC \text{ (antibiotic alone)}}$$

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al, *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, Solid Phase Peptides Synthesis, (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention includes polynucleotides encoding peptides of the invention. Exemplary polynucleotides encode peptides including SEQ ID NOs:3–21 and analogs, derivatives, amidated variations and conservative variations thereof. The peptides of the invention include SEQ ID NOs:3–21, as well as the broader groups of peptides having hydrophilic and hydrophobic substitutions, and conservative variations thereof as described above. Of course, the amino acid sequences of SEQ ID NOs:13 and 14 do not differ with the exception that the C-terminus of SEQ ID NO:14 is amidated. In addition, the amino acid sequences of SEQ ID NOs:15 and 16 do not differ with the exception that the C-terminus of SEQ ID NO:16 is amidated.

The term ≡isolated≡ as used herein refers to a polynucleotide substantially free of proteins, lipids, nucleic acids, for example, with which it is naturally associated. As used herein, ≡polynucleotide≡ refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code. Such polynucleotides are useful for the recombinant production of large quantities of a peptide of interest, such as the peptide of SEQ ID NOS:3–21.

In the present invention, the polynucleotides encoding the cationic peptides of the invention may be inserted into a recombinant ≡expression vector≡. The term ≡expression vector≡ refers to a plasmid, virus or other vehicle known in the art that has been manipulated by insertion or incorporation of cationic genetic sequences. Such expression vectors of the invention are preferably plasmids which contain a promoter sequence which facilitates the efficient transcription of the inserted genetic sequence in the host.

The expression vector typically contains an origin of replication, a promoter, as well as specific genes which allow phenotypic selection of the transformed cells. For example, the expression of the peptides of the invention can be placed under control of *E. coli* chromosomal DNA comprising a lactose or lac operon which mediates lactose utilization by elaborating the enzyme beta-galactosidase. The lac control system can be induced by IPTG. A plasmid can be constructed to contain the lac Iq repressor gene, permitting repression of the lac promoter until IPTG is added. Other promoter systems known in the art include beta lactamase, lambda promoters, the protein A promoter, and the tryptophan promoter systems. While these are the most commonly used, other microbial promoters, both inducible and constitutive, can be utilized as well. The vector contains a replicon site and control sequences which are derived from species compatible with the host cell. In addition, the vector may carry specific gene(s) which are capable of providing phenotypic selection in transformed cells. For example, the beta-lactamase gene confers ampicillin resistance to those transformed cells containing the vector with the beta-lactamase gene. An exemplary expression system for production of the peptides of the invention is described in U.S. Pat. No. 5,707,855, incorporated herein by reference.

Transformation of a host cell with the polynucleotide may be carried out by conventional techniques well known to those skilled in the art. For example, where the host is prokaryotic, such as *E. coli*, competent cells which are capable of DNA uptake can be prepared from cells harvested after exponential growth and subsequently treated by the CaCl$_2$ method using procedures well known in the art. Alternatively, MgCl$_2$ or RbCl could be used.

In addition to conventional chemical methods of transformation, the plasmid vectors of the invention may be introduced into a host cell by physical means, such as by electroporation or microinjection. Electroporation allows transfer of the vector by high voltage electric impulse, which creates pores in the plasma membrane of the host and is performed according to methods well known in the art. Additionally, cloned DNA can be introduced into host cells by protoplast fusion, using methods well known in the art. DNA sequences encoding the cationic peptides can be expressed in vivo by DNA transfer into a suitable host cell. AHost cells≅ of the invention are those in which a vector can be propagated and its DNA expressed. The term also includes any progeny of the subject host cell. It is understood that not all progeny are identical to the parental cell, since there may be mutations that occur during replication. However, such progeny are included when the terms above are used. Preferred host cells of the invention include *E. coli*, *S. aureus* and *P. aeruginosa*, although other Gram-negative and Gram-positive organisms known in the art can be utilized as long as the expression vectors contain an origin of replication to permit expression in the host.

The cationic peptide polynucleotide sequence used according to the method of the invention can be isolated from an organism or synthesized in the laboratory. Specific DNA sequences encoding the cationic peptide of interest can be obtained by: 1) isolation of a double-stranded DNA sequence from the genomic DNA; 2) chemical manufacture of a DNA sequence to provide the necessary codons for the cationic peptide of interest; and 3) in vitro synthesis of a double-stranded DNA sequence by reverse transcription of mRNA isolated from a donor cell. In the latter case, a double-stranded DNA complement of mRNA is eventually formed which is generally referred to as cDNA.

The synthesis of DNA sequences is frequently the method of choice when the entire sequence of amino acid residues of the desired peptide product is known. In the present invention, the synthesis of a DNA sequence has the advantage of allowing the incorporation of codons which are more likely to be recognized by a bacterial host, thereby permitting high level expression without difficulties in translation. In addition, virtually any peptide can be synthesized, including those encoding natural cationic peptides, variants of the same, or synthetic peptides.

When the entire sequence of the desired peptide is not known, the direct synthesis of DNA sequences is not possible and the method of choice is the formation of cDNA sequences. Among the standard procedures for isolating cDNA sequences of interest is the formation of plasmid or phage containing cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the cationic peptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single stranded form (Jay, et al., *Nuc. Acid Res.*, 11:2325, 1983).

The invention also provides a method of inhibiting the growth of bacteria including contacting the bacteria with an inhibiting effective amount of a peptide of the invention, including SEQ ID NOS:3–21 and analogs, derivatives, amidated variations and conservative variations thereof.

The term Acontacting≅ refers to exposing the bacteria to the peptide so that the peptide can effectively inhibit, kill, or lyse bacteria, bind endotoxin (LPS), or permeabilize gram-negative bacterial outer membranes, for example. Contacting may be in vitro, for example by adding the peptide to a bacterial culture to test for susceptibility of the bacteria to the peptide. Contacting may be in vivo, for example administering the peptide to a subject with a bacterial disorder, such as septic shock. AInhibiting≅ or Ainhibiting effective amount≅ refers to the amount of peptide which is required to cause a bacteriostatic or bactericidal effect. Examples of bacteria which may be inhibited include *Escherichia coli*, *Pseudomonas aeruginosa*, *Enterobacter cloacae*, *Staphylococcus typhimurium*, *Staphylococcus aureus*, *Enterobacter facaelis*, *Listeria monocytogenes*, *Corynebacterium xerosis*, *Streptococcus pyogenes*, *Streptococcus pneumoniae*, *Streptococcus mitis*, *Staphylococcuus epidermidis* and *Staphylococcus aureus* K147.

The method of inhibiting the growth of bacteria may further include the addition of antibiotics and/or lysozyme for combination or synergistic therapy. The appropriate antibiotic administered will typically depend on the susceptibility of the bacteria such as whether the bacteria is gram negative or gram positive, and will be easily discernable by one of skill in the art. Examples of particular classes of antibiotics useful for synergistic therapy with the peptides of the invention include aminoglycosides (e.g., tobramycin), penicillins (e.g., piperacillin), cephalosporins (e.g., ceftazidime), fluoroquinolones (e.g., ciprofloxacin), carbapenems (e.g., imipenem), tetracyclines and macrolides (e.g., erythromycin and clarithromycin). Further to the antibiotics listed above, typical antibiotics include aminoglycosides (amikacin, gentamicin, kanamycin, netilmicin, tobramycin, streptomycin, azithromycin, clarithromycin, erythromycin, erythromycin estolate/ethylsuccinate/gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin and mupirocin.

The peptides and/or analogues or derivatives thereof may be administered to any host, including a human or non-human animal, in an amount effective to inhibit not only growth of a bacterium, but also a virus, parasite or fungus. These peptides are useful as antimicrobial agents, antiviral agents, and antifungal agents. The peptides and/or analogues or derivatives thereof may be administered to any host, including a human or non-human animal, in an amount effective to inhibit not only growth of a bacterium, but also a virus or fungus. These peptides are useful as antimicrobial agents, antiviral agents, and antifungal agents.

In addition to being active against a broad range of pathogens, cecropin and particularly melittin have been shown to be cytotoxic to eukaryotic cells. Thus, it is envisioned that the peptides of the present invention can be used to inhibit the growth of a eukaryotic cell by contacting the eukaryotic cell with an inhibiting effective amount of a peptide of the invention. Such a method would be useful, for example, for inhibiting a cell proliferation-associated disorder in a subject having or at risk of having such a disorder. The method can involve, for example, administering to the subject a therapeutically effective amount of a peptide of the present invention to inhibit the over-growth of cells in a subject in need of such treatment. Such disorders would include, for example, neurological related disorders.

In a further embodiment, the peptides of the invention can be administered in combination with at least one chemotherapeutic agent useful for treating a cell proliferation-associated disorder, such as a neoplastic disorder. Examples of such chemotherapeutic agents include, but are not limited to, bleomycin, neocarcinostatin, suramin, doxorubicin, taxol, mitomycin C and cisplatin. Such neoplastic disorders would include, for example, neuroblastomas, glioblastomas and astrocytomas.

The peptide(s) of the invention can be administered parenterally by injection or by gradual infusion over time. The peptide can be administered intravenously, intraperitoneally, intramuscularly, subcutaneously, intracavity, or transdermally. Further methods for delivery of the peptide include orally, by encapsulation in microspheres or proteinoids, by aerosol delivery to the lungs, or transdermally by iontophoresis or transdermal electroporation. The method of the invention also includes delivery systems for administration such as microencapsulation of peptides into liposomes. Microencapsulation also allows co-entrapment of antimicrobial molecules along with the antigens, so that these molecules, such as antibiotics, may be delivered to a site in need of such treatment in conjunction with the peptides of the invention. Liposomes in the blood stream are generally taken up by the liver and spleen. Thus, the method of the invention is particularly useful for delivering antimicrobial peptides to such organs. Other methods of administration will be known to those skilled in the art.

Preparations for parenteral administration of a peptide of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Cystic fibrosis is the most common, eventually fatal, recessive genetic disease in Western society. It derives from a mutation in a single protein, CFTR, present in the membrane of certain cells in the body, including epithelial cells. The gene for this protein has been cloned and a wide variety of recessive mutations identified (although one, Δ508 is predominant). The function of CFTR has been somewhat defined although it is not known whether it functions primarily as a cyclic AMP triggered chloride channel or whether some other, unknown substrate is co-transported with chloride. Furthermore, it is not known how these genotypic defects relate to the known phenotypic abnormalities, namely malabsorption of food, pancreatic deficiencies and sterility (in subsets of patients) and predilection to lung infections. As long as lung infections are suppressed however, individuals with cystic fibrosis can lead a productive life. Thus, cystic fibrosis is not per se a lethal disease and it can to some extent be clinically managed, resulting in a life expectancy that can exceed 35 years (as compared to 2 years when cystic fibrosis was first identified).

The eventual onset of terminal lung disease is almost certainly triggered by an inability to rid the lungs of infection, primarily due to the development of resistance to one class of antibiotics after another. The continuous presence of *Pseudomonas aeruginosa* in the lungs leads to initiation of a chronic inflammatory response and to immune-complex disease. At this stage, progressive lung deterioration, probably due to host factors such as neutrophil elastase, leads to eventual death. Although Pseudomonas produces many potentially harmful virulence factors and enzymes, there is no substantive evidence that these are major contributors to death, and it is worth noting the *P.aeruginosa* in other clinical manifestations causes a rapidly progressing disease that is either suppressed by antibiotic therapy or host immunity, or kills within a few days.

The major objectives of therapy for CF patients is to promote clearance of secretions and control infection in the lung, provide adequate nutrition, and prevent intestinal obstruction. Ultimately gene therapy may be the treatment of choice. At present, the techniques for clearing pulmonary secretion are a combination of breathing exercise and chest percussion. A number of pharmacologic agents for increasing mucus clearance are being tested. N-Acetal-cysteine has not been shown to have clinically significant effects on mucus clearance and/or lung function. Agents that degrade the high concentration of DNA in CF sputum, e.g., recombinant DNAse, appear to be effective in decreasing sputum viscosity and increasing airflow during short-term administration. Experimental drugs aimed at restoring salt and water content of secretions, e.g., amiloride and triphoshpate nucleotides, are in development. In addition, standard antibiotic treatment are employed to reduce the risks of infection.

The invention provides a method of treating respiratory infections or respiratory disorders (e.g., cystic fibrosis) for example, by intranasal or aerosol administration of the peptides of the invention. Aerosol protection utilizing the peptides of the invention will result in a reduction in bacteria (see Table 9). The therapeutic management of patients with cystic fibrosis (CF) is envisioned utilizing the peptides of the invention. Chronic respiratory tract infections and pancreatic insufficiency are the major manifestations. *Pseudomonas aeruginosa* and *Staphylococcus aureus* are the most common pathogens in respiratory infections, which usually require 2–3 weeks of intravenous antibiotic therapy. Because patients with CF often have rapid clearance of both penicillins and aminoglycosides and altered apparent distribution volumes of aminoglycosides, individualized dosing has been required. Bronchodilators can be useful in improving pulmonary function. Vitamin supplementation with both the fat- and water-soluble vitamins is important in the treatment of CF. Iron supplementation may also be necessary. The use of antibiotics and replacement of pancreatic enzymes will, however, continue to be the mainstay of therapy.

The significance of *P. aeruginosa* as an emerging opportunistic infection in the tracheobronchial tree, and the rapid development of antibiotic resistance attributable to its ability to "develop genetic mutations" and alter its "morphologic appearance" has made it essential that alternate treatments be developed. Effective antibiotics in combination with peptides of the invention could be employed and the peptide and/or antibiotic in various combinations changed when specifically indicated based upon cultures of tracheobronchial secretions. Lysozyme could also be administered in combination with the peptides of the invention, either with or without antibiotics. To minimize the appearance of resistant strains, various antibiotics or combinations thereof, having different mechanisms of action are desirable along with the peptides of the invention. In addition to the peptides of the invention, antibiotics, Activase, DNase, antielastase and the like can also be administered to a subject having or at risk of having a respiratory infection.

The term "contacting≅ or Aadministering" with respect to respiratory infections or disorders shall include the administration of peptide drug to a patient in need thereof by the intrapulmonary route of administration which event may encompass one or more releases of peptide formulation over a period of time.

Formulations are preferably solutions, e.g. aqueous solutions, ethanoic solutions, aqueous/ethanoic solutions, saline solutions, microcrystalline suspensions and colloidal suspensions. Formulations can be solutions or suspensions of peptide in a low boiling point propellant. For propellant formulations, a cosolvent might be used (such as ethanol, among many other possibilities) to dissolve the peptide in the propellant (which is usually some organic compound such as an alkane or hydrofluoroalkane, but could be carbon dioxide as well as many other compounds), or surfactants might be added (such as lecithin or oleic acid, again among many others) if the peptide is not soluble in the propellant so that a suspension formulation is used instead. The peptide drug can be packaged in a dry form and mixed with water prior to administration. The peptide drug maybe kept in the form of a dry powder which is intermixed with an airflow in order to provide for particlized delivery of drug to the patient.

Regardless of the type of peptide drug or the form of the peptide drug formulation, it is preferable to create particles having a size in the range of about 0.5 to 5 microns. By creating peptide drug particles which have a relatively narrow range of size, it is possible to further increase the efficiency of the drug delivery system and improve the repeatability of the dosing.

The invention also provides a method of treating or ameliorating an endotoxemia or septic shock (sepsis) associated disorder, or one or more of the symptoms of sepsis comprising administering to a subject displaying symptoms of sepsis or at risk for developing sepsis, a therapeutically effective amount of a cationic peptide of the invention, for example, SEQ ID NOs:3–12, or analogs, derivatives, amidated variations or conservative variations thereof. The term Aameliorate≅ refers to a decrease or lessening of the symptoms of the disorder being treated. Such symptoms which may be ameliorated include those associated with a transient increase in the blood level of TNF, such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *Escherichia coli, Haemophilus influenza B, Neisseria meningitides*, staphylococci, or pneumococci. Patients at risk for sepsis include those suffering from gunshot wounds, renal or hepatic failure, trauma, burns, immunocompromised (HIV), hematopoietic neoplasias, multiple myeloma, Castleman's disease or cardiac myxoma. Methods for producing antimicrobial peptides of the invention effective for treating endotoxin-associated disorders are set forth in PCT Application Serial Number PCT/CA93/00342, incorporated herein by reference in its entirety.

The term Atherapeutically effective amount≅ as used herein for treatment of endotoxemia refers to the amount of cationic peptide used is of sufficient quantity to decrease the subject's response to LPS and decrease the symptoms of sepsis. The term Atherapeutically effective≅ therefore includes that the amount of cationic peptide sufficient to prevent, and preferably reduce by at least 50%, and more preferably sufficient to reduce by 80%, a clinically significant increase in the plasma level of TNF. The dosage ranges for the administration of cationic peptide are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. A decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of cationic peptide, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey, et al. (*Nature*, 330:662, 1987).

A patient who exhibits the symptoms of sepsis may be treated with an antibiotic in addition to the treatment with cationic peptide. Typical antibiotics include an aminoglycoside, such as gentamicin or a beta-lactam such as penicillin, or cephalosporin or any of the antibiotics as previously listed above. Therefore, a preferred therapeutic method of the invention includes administering a therapeutically effective amount of cationic peptide substantially simultaneously with administration of a bactericidal amount of an antibiotic. Preferably, administration of cationic peptide occurs within about 48 hours and preferably within about 2–8 hours, and most preferably, substantially concurrently with administration of the antibiotic.

The term Abactericidal amount≅ as used herein refers to an amount sufficient to achieve a bacteria-killing blood concentration in the patient receiving the treatment. The bactericidal amount of antibiotic generally recognized as safe for administration to ahuman is well known in the art, and as is known in the art, varies with the specific antibiotic and the type of bacterial infection being treated.

Because of the antibiotic, antimicrobial, and antiviral properties of the peptides, they may also be used as preservatives or sterilants of materials susceptible to microbial or viral contamination. The peptides of the invention can be utilized as broad spectrum antimicrobial agents directed toward various specific applications. Such applications include use of the peptides as preservatives in processed foods (organisms including Salmonella, Yersinia, Shigella), either alone or in combination with antibacterial food additives such as lysozymes; as a topical agent (Pseudomonas, Streptococcus) and to kill odor producing microbes (Micrococci). The relative effectiveness of the cationic peptides of the invention for the applications described can be readily determined by one of skill in the art by determining the sensitivity of any organism to one of the peptides.

In another embodiment, the invention provides a method for accelerating wound healing in a subject by administering to the wound a therapeutically effective amount of a composition which contains antimicrobial cationic peptides. The peptides of the invention are valuable as therapeutics in cases in which there is impaired healing of a wound due to pathogenic microbial infections, or there is a need to augment normal healing mechanisms by including such peptides.

Agents which promote wound repair can further be included in such compositions to augment wound healing. Such agents include members of the family of growth factors such as insulin-like growth factor (IGF-I), platelet-derived growth factor (PDGF), epidermal growth factor (EGF), transforming growth factor beta (TGF-β) and basic fibroblast growth factor (bFGF). More preferably, the agent is transforming growth factor beta (TGF-β) or other member of the TGF-β superfamily. Antimicrobial peptide compositions are prepared by combining, in pharmaceutically acceptable carrier substance, e.g., inert gels or liquids, a purified antimicrobial peptide(s) of the invention.

As used herein, a Atherapeutically effective amount≈ of a composition containing an antimicrobial peptide of the invention with or without an active biologic agent means that which stimulates or induces cell growth. While not wanting to be bound to a particular theory, a therapeutically effective amount is beneficial for augmenting tissue repair by promoting tissue regeneration while simultaneously inhibiting or preventing pathogenic microbial growth. Diseases, infections, disorders or ailments benefitting from such modulation of tissue growth and inhibition of pathogenic microbial growth include, but are not limited to, tissue repair subsequent to traumatic injuries, conditions including arthritis, osteoporosis and other skeletal disorders, damage due to chronic bronchitis, damage due to smoke inhalation, damage due to a host immune response, damage due to fungal, bacterial, viral, protozoan, and parasitic diseases, and burns, for example. Because these problems are likely due to a poor growth response of the fibroblasts, stem cells, chondrocytes, osteoblasts or fibroblasts at the site of injury, the addition of an active biologic agent that stimulates or induces growth of these cells is beneficial. The term Ainduce≈ or Ainduction≈ as used herein, refers to the activation, stimulation, enhancement, initiation and or maintenance of the cellular mechanisms or processes necessary for the formation of any of the tissue, repair process or development as described herein.

In another aspect, the invention is useful for revitalizing scar tissue resulting from microbial (e.g., fungal, parasitic, viral infection, bacterial infection or protozoan infections) injuries due to surgical procedures, irradiation, laceration, toxic chemicals or burns, for example. The term Ascar tissue≈ means fibrotic or collagenous tissue formed during the healing of a wound. For example, antimicrobial peptides can be included in a controlled release matrix which can be positioned in proximity to damaged tissue thereby promoting regeneration and revascularization of such tissue. The term Acontrolled release matrix≈ means any composition which allows the slow release of a bioactive substance which is mixed or admixed therein. The matrix can be a solid composition, a porous material, or a semi-solid, gel or liquid suspension containing bioactive substances. The term Abioactive material≈ means any composition that will modulate tissue repair when used in accordance with the method of the present invention. The bioactive materials/matrix can be introduced by means of injection, surgery, catheters or any other means suitable for modulating tissue repair.

It is envisioned that the method of the invention can be used to aid wound repair in guided tissue regeneration (GTR) procedures. Such procedures are currently used by those skilled in the medical arts to accelerate wound healing following invasive surgical procedures. Typically, nonresorbable or bioabsorbable membranes are used to accelerate wound healing by promoting the repopulation of the wound area with cells which form the architectural and structural matrix of the tissue. For example, the method of the invention can be used in aiding periodontal tissue regeneration in a human or lower animal by placing a composition containing a bioresorbable polymer, leachable solvent, and antimicrobial peptides at a site in need of periodontal tissue regeneration in a human or other mammal such that the composition is effective for aiding tissue regeneration by releasing a therapeutically-effective amount of antimicrobial peptides at the site thereby inhibiting or preventing pathogenic microbial growth.

In another aspect, the invention can be useful for the purposes of promoting tissue growth during the process of tissue engineering. As used herein, Atissue engineering≈ is defined as the creation, design, and fabrication of biological prosthetic devices, in combination with synthetic or natural materials, for the augmentation or replacement of body tissues and organs. Thus, the present method can be used to augment the design and growth of human tissues outside the body for later implantation in the repair or replacement of diseased tissues. For example, antimicrobial peptides may be useful in promoting the growth of skin graft replacements which are used as a therapy in the treatment of burns by preventing or inhibiting pathogenic microbial growth.

In another embodiment, a transgenic non-human animal, such as a fish, expressing antimicrobial peptides of the invention is envisioned. Such a fish, for example, would be resistant to various pathogenic organisms including, for example, *Staphylococcus aureus, Listeria monocytogenes, Corynebacterium xerosis, Streptococcus pyogenes, Streptococcus pneumoniae, Streptococcus mitis, Staphylococcuus epidermidis, Escherichia coli, Pseudomonas aeruginosa, Enterobacter facaelis, Salmonella typhimurium, Salmonella typhimurium* phoP phoQ, *Aeromonas salmonicida, Vibrio anguillarum* and *Enterobacter cloacae.*

It is envisioned that any aquatic animal susceptible to bacterial, fungal, parasitic, protozoan, or viral infection, for example, is useful for the expression of a transgene of the invention. Preferably, such aquatic animals would include those used as a food source by humans. Such animals would include, for example, fish selected from the group consisting of salmonids (e.g., salmon), scombrids (e.g., tuna), portunids (e.g., crab), pleuronectids (e.g., flounder), lutjanids (e.g., snapper) and ictalurids (e.g., catfish). In addition, a transgenic aquatic animal of the invention can be used as a source of antimicrobial cationic peptides useful for the treatment of human pathogenic microbial infections. For example, antimicrobial cationic peptides of the invention can be expressed in, and harvested from, transgenic fish. Thus, transgenic fish the present invention provide a rapidly growing and easily harvestable source of antimicrobial peptides useful for treating human pathologies.

Exemplary peptides useful for inhibiting microbial infection or growth in a transgenic fish, or inhibiting microbial infection or growth in humans, include:

| | |
|---|---|
| GWGSFFKLKAAHVGKHVGKAALTHYL-NH2; | (SEQ ID NO:14) |
| KGWGSFFKAAHVGKHVGKAALTHYL; | (SEQ ID NO:15) |
| KGWGSFFKKAAHVGKHVGKAALTHYL-NH2; | (SEQ ID NO:16) |
| ALWKTMLKKAAHVGKHVGKAALTHYL-NH2; | (SEQ ID NO:17) |
| SIGSAFKKAAHVGKHVGKAALTHYL-NH2; | (SEQ ID NO:18) |
| GWGSFFKKAAHVGKHVGKAALGAAARRRK; | (SEQ ID NO:19) |
| ALWKTMLKKAAHVGKHVGKAALGAAARRRK; | (SEQ ID NO:20) |
| SIGSAFKKAAHVGKHVGKAALGAAARRRK; | (SEQ ID NO:21) | and analogs, derivatives, amidated variations and conservative variations thereof.

In another embodiment of the invention, novel constructs may be prepared containing nucleic acid sequences encoding the antimicrobial peptides of the invention. Such constructs are useful to produce transgenic fish that express non-native cationic peptides resulting in fish that are resistant to pathogenic organisms including bacteria, fungi, parasites and viruses.

In accordance with a further embodiment of the invention, a method for producing transgenic fish expressing antimicrobial peptides of the invention by introducing into fish eggs nucleic acid encoding cationic peptides of the invention resulting in fish that are resistant to pathogenic organisms, is provided.

This method of producing enhanced fish immunity offers some advantage over direct administration of the antimicrobial cationic peptide to the fish. Exposure to the peptide may have to be continued over considerable periods of time depending on the fish species. Repeated handling of fish for sequential treatments with peptides is, however, likely to induce stress syndrome. Producing a transgenic fish expressing the peptide obviates the need for such treatments and avoids the possibility of inducing stress syndrome.

A transgene encoding a peptide of the invention operatively linked to a suitable upstream promoter and a suitable downstream termination sequence can be ligated into a plasmid to form a DNA construct suitable for transfecting, for example, a fish egg, and producing a transgenic fish.

Suitable promoters include RSV and TK, for example. A promoter obtained from fish is preferred for use in fish. Suitable fish promoters include SH, PRL, and STH. The transcription termination sequence of the construct may be that associated with the selected DNA or may be another suitable transcription termination sequence. A fish transcription termination sequence is preferred. Thus, in one aspect of the invention, a DNA construct comprises a selected DNA in accordance with the invention encoding the peptide or peptides to be expressed in the fish, operatively linked to a fish gene promoter and a fish gene transcription termination sequence in a suitable plasmid (e.g., pUC 18 or pUC 19, STRATAGENE, La Jolla Calif.). Suitable methods for introducing the construct into fish to produce transgenic fish are described by Hew and Fletcher (Eds.) in ATransgenic Fish≈, World Scientific Press, pp 1–274, 1992, incorporated herein by reference in its entirety.

A preferred method is microinjection of the construct containing the selected DNA in accordance with the invention into fertilized, but not activated, teleost eggs. Fertilized teleost eggs can be injected relatively easily through the micropyle using a very find glass needle (2–3 pm) (Fletcher, CAN. *J. Fish Aquat. Sci.*, 45:252–357, 1988). Microinjection through the micropyle facilitates the procedure by 1) allowing for easier access to the egg cytoplasm and 2) providing a means of locating and introducing the vector in close proximity to the yet uncombined male and female pronuclei thereby increasing the chances of single cell genomic integration. Other methods of preparation of transgenic fish include introducing the vector by electroporation (Neuman, *EMBO J.*, 1:842–845, 1982) $CaCl_2$ precipitation, or lipofection (Felgner, *Proc. Natl. Acad. Sci.*, 84:7413–7417, 1987).

In accordance with a further embodiment of the invention, a method is provided for identifying a transgenic fish carrying a novel DNA construct in accordance with the invention. As described above, a DNA construct is created comprising a novel DNA coding for an antimicrobial peptide, ligated between a promoter and a transcription termination sequence (TTS). The genome of a non-transgenic fish lacks any portion of the nucleic acid encoding the cationic peptides of the invention. The presence of nucleic acid encoding the non-native cationic antimicrobial peptide in a transgenic fish represents a unique sequence which may be used to identify the transgenic fish. For example, oligonucleotide primers which hybridize specifically to the unique sequence encoding a cationic peptide can be designed and used to amplify the sequence. As will be understood by those skilled in the art, a variety of primers may be made by conventional methods and used in this method for identification of transgenic fish, provided that at least one primer is generated to a unique site in the nucleic acid sequence encoding a cationic peptide of the invention. For analysis, DNA may be obtained from a variety of fish tissues, including blood and fin tissue.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Synthesis of Novel Cationic Antimicrobial Peptides

Cationic peptides were synthesized at the University of British Columbia service facility. The amino acid sequence of the peptides are shown in Table 1.

TABLE 1

Peptide Amino Acid Sequences and Characteristics

| Peptide | Amino Acid Sequence | Length | Charge | % Hydrophobicity | SEQ ID NO: |
|---|---|---|---|---|---|
| CEMA | KWKLFKKIGIGAVLKVLTTGLPAKLTK | 28 | +6 | 64 | 1 |
| CP-29 | KWKSFIKKLTTAVKKVLTTGLPALIS | 26 | +6 | 50 | 2 |
| CM-1: | KWKSFIKKLTSAAKKVVTTAKPLALIS | 27 | +7 | 56 | 3 |
| CM-2: | KWKSFIKKLTKAAKKVVTTAKKPLIV | 26 | +9 | 54 | 4 |
| CM-3: | KWKKFIKSLTKSAAKTVVKTAKKPLIV | 27 | +9 | 52 | 5 |
| CM-4: | KWKLFKKIGIGAVLKVLKVLTTGLPALKLTLK | 32 | 7 | 66 | 6 |
| CM-5: | KLFKKIGIGAVLKVLKVLTTGLPALKLTLK | 30 | +6 | 65 | 7 |
| CM-6: | KWKFKKIGIGAVLKVLKVLTTGLPALKLTLK | 31 | +7 | 63 | 8 |
| CM-7: | KLWKLFKKIGIGAVLKVLKVLTTGLPALKLTLK | 33 | +7 | 66 | 9 |
| CPα1: | KWKSFIKKLTSAAKKVTTAAKLPLTK | 25 | +8 | 44 | 10 |
| CPα2: | KWKKFIKKIGIGAVLKVLTTGLPALKLTKK | 30 | +9 | 60 | 11 |
| CPα3: | KKWKKFIKKIGIGAVLTTPGAKK | 23 | +8 | 57 | 12 |

EXAMPLE 2

Susceptibility Testing

A method which employed polypropylene microtiter trays in a broth microdilution assay was developed. Theses studies showed that several of the peptides had good antimicrobial activity (Table 2).

TABLE 2

MIC (μg/ml) of the antimicrobial peptides against a variety of bacteria

| Peptide | P. aeruginosa | E. coli | S. epidermis | S. aureus | S. aureus K147 |
|---|---|---|---|---|---|
| CEMA | 3 | 2 | 3 | 4 | 3 |
| CP-29 | 6 | 2 | 5 | 19 | 11 |
| CM1 | 5 | 1 | 21 | 64 | 32 |
| CM2 | 3 | 1 | 5 | >64 | >64 |
| CM3 | 5 | 1 | 16 | >64 | >64 |
| CM4 | 4 | 4 | 4 | 8 | 8 |
| CM5 | 16 | 4 | 11 | >64 | 64 |
| CM6 | 8 | 2 | 8 | 32 | 32 |
| CM7 | 8 | 2 | 4 | 8 | 4–8 |
| CPα1 | ≧64 | 1.5 | — | >64 | >64 |
| CPα2 | 6 | 2 | — | 16 | 16 |
| CPα3 | ≧64 | 4 | — | >64 | >64 |

The data in this table represent an average of three separate experiments.

EXAMPLE 3

Synergy with Conventional Antibiotics

It has been shown that some peptides demonstrated synergy with conventional antibiotics. To test whether the peptides of the invention synergize with various antibiotics, the following method was employed. Fractional Inhibitory Concentration (FIC) was used to determine synergy of peptides combined with antibiotics (e.g., carbenicillin/ciprofloxacin) against *Pseudomonas aeruginosa*. The following methodology was followed:

(1) Determination of MIC of cationic peptides (MIC A):

100 μl Mueller Hinton broth (MHB) was added per well 12.5 μl of 10× test concentration peptide was added per well to get final peptide concentration of e.g., 128, 64, 32, . . . 0.025 μg/ml from row 1 to 11;

10 μl of $10^{-4}$ dilution of overnight bacterial culture was added per well.

(2) Determination of MIC of Carbenicillin/Ciprofloxacin (MIC B):

100 μl MHB was added per well;

100 μl of 2× test concentration of antibiotic was added in the first well of the row, and doubling dilutions performed across the plate from column 1 to 11;

10 μl of $10^{-4}$ dilution of overnight bacterial culture was added per well.

(3) Determination of MIC of antibiotics (B) when combined with peptides at concentration A:

100 μl MHB was added per well;

100 μl Carbenicillin (512 μg/ml) or Ciprofloxacin (8 μg/ml) was added in each well of column 1; doubling dilutions were performed across the plate;

100 μl of the peptide was added in all wells of row 1, mixed, and 100 μl withdrawn and added to row 2, etc., creating a checkerboard titration.

10 μl of $10^{-4}$ dilution of overnight culture was added per well;

plates were incubated at 37EC for 18–24 hours. Combination MIC values A and B were taken as the lowest concentration of drug that reduced bacterial growth by more than 50% in any given column.

(4) FIC index=FICA+FICB=(A)/MIC A+(B)/MIC B. An FIC index of approximately 0.5 or less indicates synergy; 1.0 reflects additivity; and >1.0 indicates antagonism.

Some synergy (bold lines) was observed with these cationic peptides (Tables 3–6). Good synergy was seen with isolated peptides and naladixic acid or carbenicillin, and in no case was antagonism observed.

TABLE 3

Synergy study of cationic peptides combined with Carbenicillin (Carb) against the β-lactamase derepressed mutant (H547) of *P. aeruginosa*

| Peptides | MIC A MIC of Peptides | (A) Peptide doses together with Carb | MIC B MIC of Carb | (B) MIC of Carb when combined with peptide | FIC index |
|---|---|---|---|---|---|
| CM1 | 16 | 2 | 64 | 64 | FICB |
| CM2 | 4 | .5 | 64 | 64 | FICB |
| CM3 | 2 | .5 | 64 | 32 | 0.75 |
| CM4 | 4 | 1 | 64 | 64 | FICB |
| CM5 | 32 | 4 | 64 | 16 | 0.38 |
| CM6 | 2 | 1 | 64 | 64 | FICB |
| CM7 | 32 | 2 | 64 | 64 | FICB |
| CP-α1 | 16 | 4 | 64 | 32 | 0.75 |
| CP-α2 | 2 | 1 | 64 | 32 | 1.0 |
| CP-α3 | 16 | 4 | 64 | 32 | 0.75 |

FIC index = FICA + FICB = (A)/MIC A = (B)/MIC B.

TABLE 4

Synergy study of cationic peptides combined with nalidixic acid (Nal) against the *P. aeruginosa* gyrase mutant (Nal A, H374)

| Peptides | MIC A MIC of Peptides | (A) Peptide doses together with Nal | MIC B MIC of Nal | (B) MIC of Nal when combined with peptide | FIC index |
|---|---|---|---|---|---|
| CP-α1 | 8 | 1 | 3200 | 800 | 0.38 |
| CP-α2 | 4 | 1 | 3200 | 800 | 0.50 |
| CP-α3 | 8 | 1 | 3200 | 800 | 0.50 |

TABLE 5

Synergy study of cationic peptides combined with ciprofloxacin (Cipro) against the mutant (Nal B, H744) of *P. aeruginosa*

| Peptide | MIC A MIC of Peptides | (A) Peptide doses together with Cipro | MIC B MIC of Cipro | (B) MIC of Cipro when combined with peptide | FIC index |
|---|---|---|---|---|---|
| CM1 | 2 | 1 | .25 | .25 | FICB |
| CM2 | 1 | .5 | .25 | .25 | FICB |
| CM3 | 2 | .5 | .25 | — | — |
| CM4 | 4 | 1 | .25 | .125 | .75 |
| CM5 | 4 | 1 | .25 | .125 | .75 |
| CM6 | 1 | 1 | .25 | .125 | FICA |
| CM7 | 16 | 2 | .25 | .125 | .63 |
| CPα1 | 8 | 1 | .25 | .125 | .63 |
| CPα2 | 2 | 1 | .25 | .125 | .75 |
| CPα3 | 4 | 1 | .25 | .125 | .75 |

TABLE 6

Synergy study of cationic peptides combined with nalidixic acid (Nal) against a *P. aeruginosa* efflux mutant (Nal B, H744)

| Peptides | MIC A MIC of Peptides | (A) Peptide doses together with Nal | MIC B MIC of Nal | (B) MIC of Nal when combined with peptide | FIC index |
|---|---|---|---|---|---|
| CPα1 | 8 | 1 | 3200 | 400 | 0.38 |
| CPα2 | 4 | 0.5 | 3200 | 800 | 0.63 |
| CPα3 | 4 | 1 | 3200 | 400 | 0.50 |

Synergy studies (Checkerboard titration) were also performed with hen white lysozyme, an antibacterial substance used in the food industry (Tables 6A and 6B).

TABLE 6A

Lowest cationic peptide and lysozyme concentrations (μg/ml) showing synergy

| | E. coli | | Salmonella typhi | | P. aeruginosa (H103) | |
|---|---|---|---|---|---|---|
| | Lowest [CP] | Lowest [Lyso] | Lowest [CP] | Lowest [Lyso] | Lowest [CP] | Lowest [Lyso] |
| CM1 | 0.041 | 7.8 | 0.531 | 31.3 | 0.65 | 7.8 |
| CM2 | 0.081 | 7.8 | 2.61 | 31.3 | 1.3 | 7.8 |
| CM3 | 0.041 | 15.6 | 2.61 | 250 | 1.3 | 15.6 |
| CM4 | 1.3 | 7.8 | 2.61 | 7.8 | 2.6 | 250 |
| CM5 | 1.3 | 7.8 | 10.4 | 62.5 | 10.4 | 125 |
| CM6 | 0.326 | 7.8 | 5.21 | 7.8 | 5.21 | 125 |
| CM7 | 0.65 | 7.8 | 2.61 | 15.6 | 2.6 | 250 |
| CPα1 | 0.65 | 7.8 | 41.7 | 125 | 5.21 | 7.8 |
| CPα2 | 0.65 | 7.8 | 2.61 | 125 | 10.4 | 62.5 |
| CPα3 | 0.65 | 62.5 | — | — | 1.3 | 7.8 |

TABLE 6B

FICs for combinations of cationic peptides and lysozyme

| Peptide | E. coli | Salmonella typhi | P. aeruginosa (H103) |
|---|---|---|---|
| CM1 | 0.19 | 0.53 | 0.28 |
| CM2 | 0.25 | 0.53 | 0.37 |
| CM3 | 0.31 | 0.75 | 0.50 |
| CM4 | 0.07 | 0.50 | 0.75 |
| CM5 | 0.27 | 0.56 | 0.63 |
| CM6 | 0.08 | 0.50 | 0.63 |
| CM7 | 0.31 | 0.52 | 0.75 |
| CPα1 | 0.31 | 0.63 | 0.28 |
| CPα2 | 0.31 | 0.63 | 0.56 |
| CPα3 | 0.31 | Confluent | 0.08 |

EXAMPLE 4

Anti-endotoxin Activity

LPS (endotoxin) binding was examined by the dansyl polymyxin binding assay. All peptides bound to LPS (FIG. 1). The anti-endotoxic activity of the peptides was tested in the murine cell line RAW 264.7 which was obtained from the ATCC (ATCC #TIB-71), (Rockville, Md.). TNF induction experiments with LPS were performed as described by Kelly et al (*Infect. Immun.*, 59:4491–6, 1991). Briefly, Dulbecco's modified Eagle medium was aspirated from RAW 264.7 cells grown overnight in 24-well tissue culture plates after seeding with $10^6$ cells per ml per well and replaced with fresh medium. LPS at a final concentration of 100 ng/ml, was incubated with the cells for 6 hr. at 37° C. in 5% $CO_2$ prior to assaying for cytokine production. At the same time as LPS addition, cationic peptides were added at a final concentration of 20 μg/ml. All assays were performed three times with similar results.

TNF was measured in cell culture supernatants and mouse serum on the basis of cytoxicity for L929 fibroblast cells. Periodic controls in which cytotoxicity was neutralized with monoclonal antibodies against TNF-α and TNF-β (antibodies LP400 and 1221–00; Genzyme Corp., Cambridge, Mass.) indicated that TNF was solely responsible for toxicity. TNF activity was expressed in units as the reciprocal of the dilution of TNF that caused 50% cytotoxicity of L929 cells, as computed using the ELISA+program (Meddata Inc, New York, N.Y.). For the current study, one unit of TNF corresponded to 62.5 pg/ml of recombinant murine TNF (Genzyme Corp.) IL-6 production was measured by ELISA with specific antibody.

Figure 2:
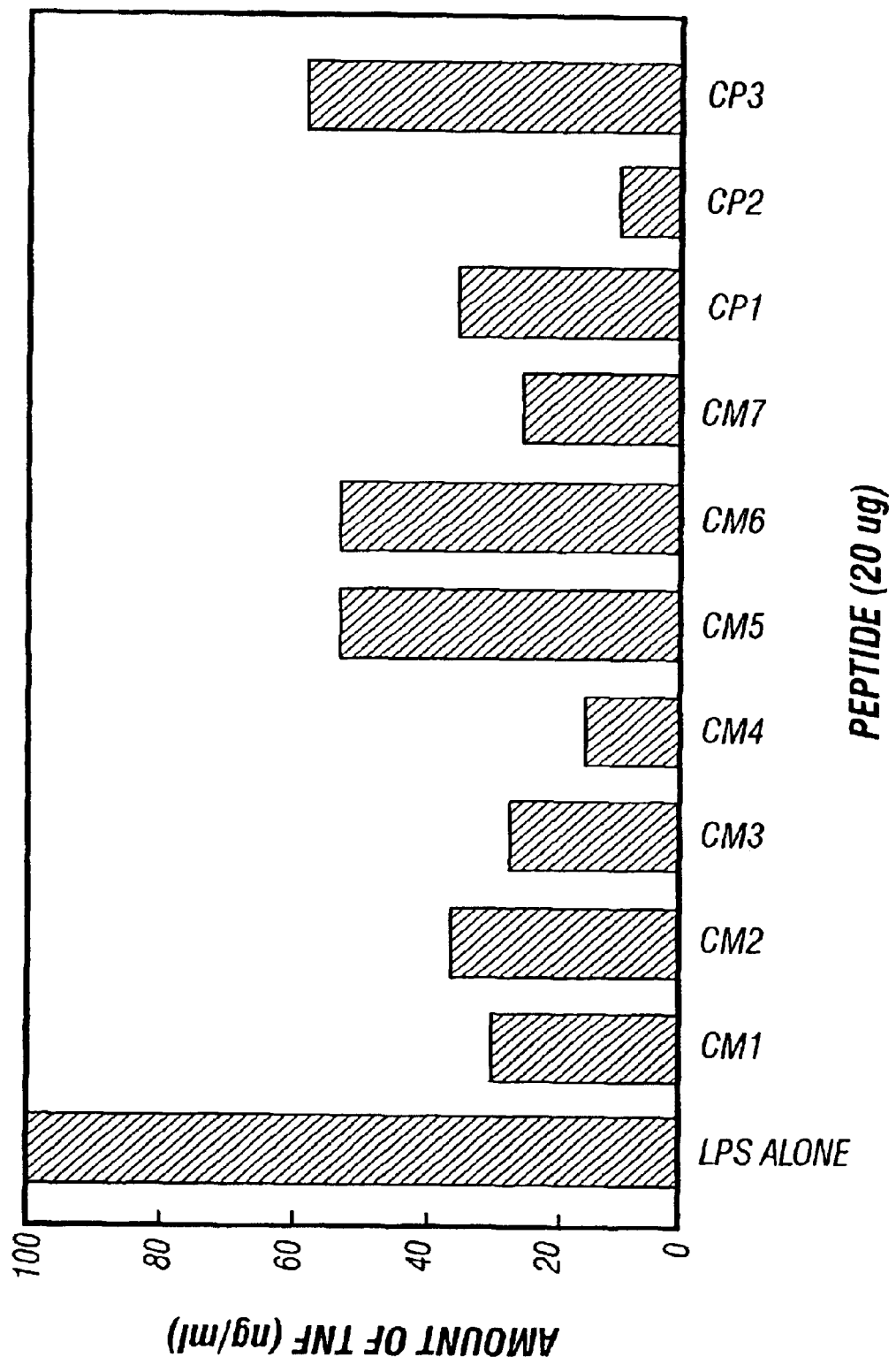
FIG. 2 is a bar graph which shows the result of inhibition of TNF production by RAW macrophage cell lines and is the mean of three experiments (performed in duplicate). The data shows that all of the peptides utilized can neutralize endotoxin from E.coli with certain peptides being clearly better than others, especially Cpα2 and CM4.
Figure 3:
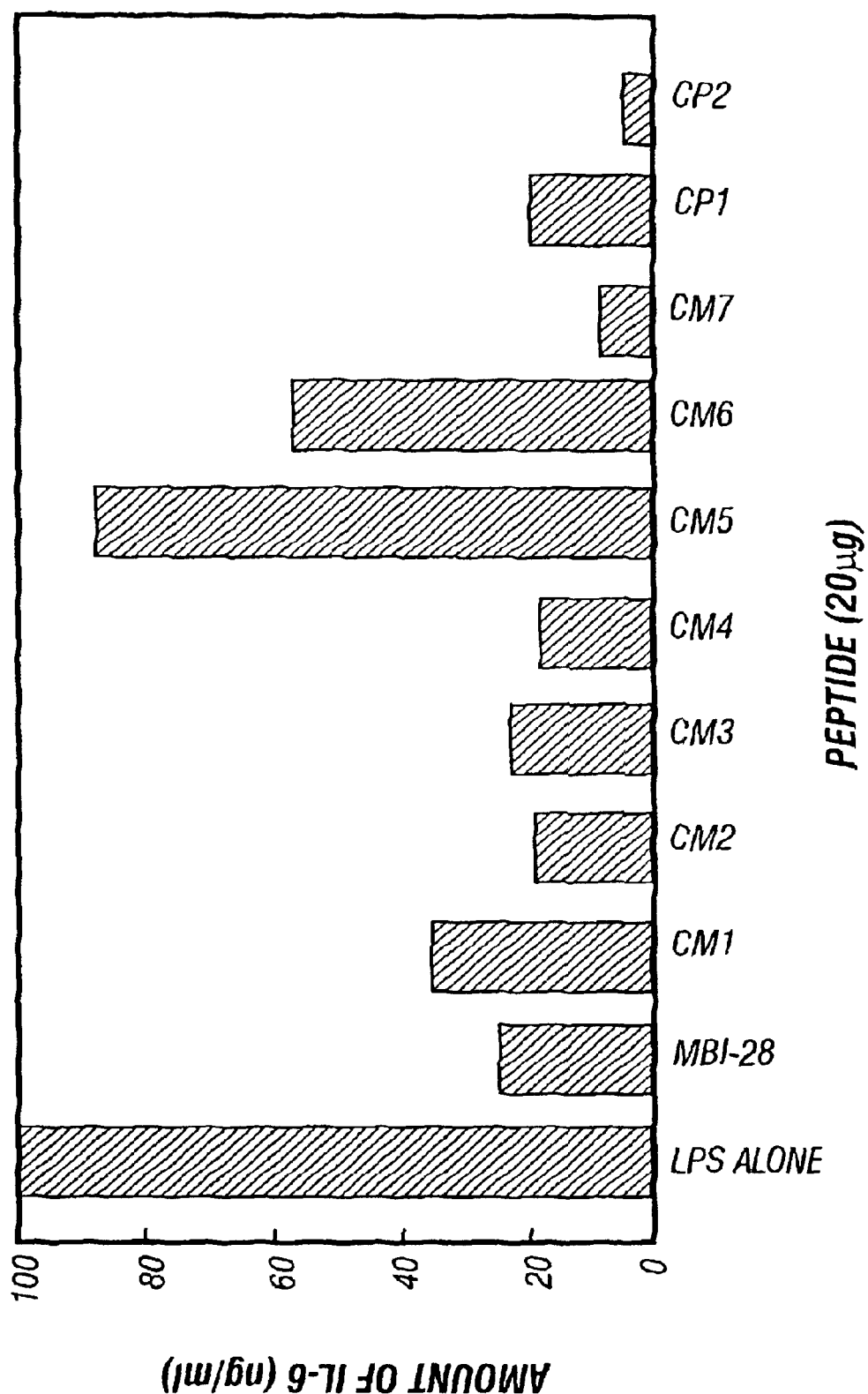
FIG. 3 is a bar graph which shows that some of the peptides were superior in their ability to suppress IL-6 production, particularly Cpα2 and CM7.

FIG. 2 shows the result of inhibition of TNF production by RAW macrophage cell lines and are generally the means of three experiments (done in duplicate). The data shows that all of the peptides utilized can neutralize endotoxin from E.coli, with certain peptides being clearly better than others, especially Cpα2 and CM4. Although these experiments were done with E. coli LPS, additional experiments showed that they reflect the data achieved with P. aeruginosa LPS. Other controls showed that the peptides themselves did not induce TNF. The cytokine IL-6 is also produced as a response to endotoxin treatments in animals and macrophage cell lines. FIG. 3 demonstrates that some of the peptides were clearly superior in their ability to suppress IL-6 production, especially CPα2 and CM7.

To confirm this in vivo, endotoxic shock was induced by intraperitoneal injection of 10 μg of E.coli 0111:B4 LPS in phosphate-buffered saline (PBS; pH 7.2) into galactosamine-sensitized 8- to 10- week old female CD-1 mice (5 per group). In experiments involving peptides, 200 μg in 100 μl of sterile water was injected at separate intraperitoneal sites within 10 min of LPS injection. Survival was monitored at 24 hours post injection. The result (Table 8) showed a mild protective effect of some of the peptides, although none was effective as SEQ ID NO:1 in these dosages.

TABLE 7

Protective effect of cationic peptides against lethal endotoxemia in galactosamine-sensitized mice

| Peptide (200 μg) | Mortality (%) |
| --- | --- |
| No peptide | 100 |
| CEMA | 0 |
| CM1 | 100 |
| CM2 | 80 |
| CM3 | 80 |
| CM4 | 80 |
| CM5 | 80 |
| CM6 | 100 |
| CM7 | 100 |

Protection of Neutropenic CD-1 Mice by Cationic Peptides

CD-1 mice were induced to be neutropenic via 3 intraperitoneal injections of cyclophosphamide (150 μg/kg/per injection) every another day. Immediately after the third administration of cyclophosphamide, the mice were challenged by intraperitoneal injection of Pseudomonas aeruginosa strain M2 (200–300 organisms/mouse). Cationic peptides (200 μg per mouse=8 mg/kg) in 100 μl buffered citrate were injected intraperitoneally at 30 min (single dose) or 30 min and 16 hrs (double dose) post bacterial challenge, respectively. The data were the average values of 2 individual experiments. PBS was used as a control. The bolded columns demonstrate better peptide protection than the CP26 and CP29 (SEQ ID NO:25 and SEQ ID NO:2, respectively) controls. In general single dose protection studies gave better protection than double dose experiments. Protection in non-neutropenic mice was not as impressive but the same peptides showed as good or better killing than SEQ ID NO:25.

TABLE 8

Protection of Neutropenic CD-1 Mice by Cationic Peptides

| Peptide | Doses | Mice Tested | 16 hr | 24 hr | 41 hr | 48 hr | 64 hr | 72 hr | 96 hr |
| --- | --- | --- | --- | --- | --- | --- | --- | --- | --- |
| PBS | | 12 | 12 | 12 | 5 | 4 | 1(8) | 1(8) | 1(8) |
| CM2 | Single | 15 | 15 | 15 | 13 | 12 | 11(73) | 11(73) | 10(66) |
| CM3 | Single | 15 | 15 | 15 | 14 | 13 | 12(80) | 11(73) | 11(73) |
| CM4 | Single | 15 | 15 | 15 | 9 | 3 | 1(6) | 1(6) | 1(16) |
| CM6 | Single | 15 | 15 | 15 | 13 | 11 | 9(60) | 9(60) | 7(46) |
| CM7 | Single | 15 | 15 | 15 | 13 | 13 | 12(80) | 11(73) | 11(73) |
| CPα2 | Single | 15 | 15 | 15 | 13 | 13 | 13(86) | 12(80) | 12(80) |
| CP26 | Single | 8 | 8 | 8 | 6 | 4 | 3(37) | 3(37) | 3(37) |
| CP29 | Single | 8 | 8 | 8 | 7 | 6 | 4(50) | 4(50) | 3(37) |
| CM2 | Double | 14 | 14 | 14 | 10 | 7 | 7(50) | 7(50) | 6(42) |
| CM3 | Double | 13 | 13 | 13 | 11 | 11 | 10(76) | 10(76) | 8(61) |
| CM4 | Double | 14 | 14 | 14 | 7 | 2 | 2(14) | 2(14) | 2(14) |
| CM6 | Double | 14 | 14 | 14 | 11 | 9 | 6(42) | 6(42) | 5(35) |
| CM7 | Double | 12 | 12 | 12 | 8 | 6 | 5(41) | 5(41) | 5(41) |
| CP-α* | Double | 13 | 13 | 13 | 12 | 9 | 6(46) | 6(46) | 5(38) |

CP 29, NH$_2$-KWKSFIKKLTTAVKKVLTTGLPALIS-COOH (SEQ ID NO:2)
CP 26, NH$_2$-KWKSFIKKLTSAAKKVVTTAKPLISS-COOH (SEQ ID NO:25)
CP28 or CEMA, (NH$_2$-KWKLFKKIGIGAVLKVLTTGLPALKLTK-COOH (SEQ ID NO:1)

EXAMPLE 5

Fifteen animals were utilized in these experiments (5 animals in each of three groups). All animals were inoculated intratracheal with 10$^4$ Pseudomonas aeruginosa PAO in agar beads. Three days following inoculation, rats were exposed to aerosol preparations from and Aero-Tech II nebulizer (CIS-US, Bedford, Mass.). The nebulizer was operated at 45 psi, with a flow rate of 10 L/min and contained 10 ml of the preparation to be aerosolized. The 10 ml volume was dispensed in 25–30 minutes. Animals were treated once daily for three days; control animals received daily exposure to 10 mls of 10 mM sodium citrate (pH 7.0); one treatment group received daily exposure to 10 mls of 10 mM sodium citrate (pH 7.0) containing 5 mg/ml of CM3; one treatment group received daily exposure to 10 mls of 10 mM sodium citrate (pH 7.0) containing 5 mg/ml of Cpα2. Animals were sacrificed on day 3, at one hour following the last exposure. The lungs of the treatment and control animals were removed for quantitative culture. Table 9 shows the results in colony forming units (CFU).

TABLE 9

Efficacy of cationic peptides in treating chronic
*Pseudomonas aeruginosa* lung infections in rats.

| Peptide | Mean Colony Forming Units +/− S.D. |
|---|---|
| Untreated Control | $1.2 \times 10^6$ +/− $9.5 \times 10^5$ |
| CM3 Treated | $7.4 \times 10^4$ +/− $6.7 \times 10^{4*}$ |
| CPα2 Treated | $6.8 \times 10^4$ +/− $3.6 \times 10^{4*}$ |

*Significantly different from control (p < 0.001), unpaired t test.

EXAMPLE 6

Pleurocidin Analogs

The second set of peptides were designed based on fish peptides (Table 10) for use in human health and/or transgenic fish construction. Table 10 includes several peptides with either a common core structure or a C-terminus common to dermaseptin (Mor et al., *Biochemistry* 30:8824–34, 1991).

TABLE 10

Sequences of Peptide Constructs

| Peptide | Amino Acid Sequence | Length | Net Charge | SEQ ID NO: |
|---|---|---|---|---|
| P-0 | GWGSFFKKAAHVGKHVGKAALTHYL | 25 | +4 | 13 |
| P-CN | GWGSFFKKAAHVGKHVGKAALTHYL-NH2 | 25 | +4 | 14 |
| P-1 | KGWGSFFKKAAHVGKHVGKAALTHYL | 26 | +5 | 15 |
| P-1-CN | KGWGSFFKKAAHVGKHVGKAALTHYL-NH2 | 26 | +5 | 16 |
| P-DER | ALWKTMLKKAAHVGKHVGKAALTHYL-NH2 | 26 | 5 | 17 |
| P-CER | SIGSAFKKAAHVGKHVGKAALTHYL-NH2 | 25 | 4 | 18 |
| P-M | GWGSFPKKAAHVGKHVGKAAL-GAAARRRK | 29 | 8 | 19 |
| DER-M | ALWKTMLKKAAHVGKHVGKAAL-GAAARRRK | 30 | 9 | 20 |
| CER-M | SIGSAFKKAAHVGKHVGKAAL-GAAARRRK | 29 | 8 | 21 |
| M-0 | RQRVEELSKFSKKGAAARRRK | 21 | 7 | 22 |
| DER | ALWKTMLKKLGTMALHAGKAAL-GAAADTISQTQ | 33 | 3 | 23 |
| CER | SIGSAFKKALPVAKKIGKAALPIA-KAALP | 29 | 4 | 24 |

Known peptides include P-0 = flounder pleurocidin (Cole et al., J. Biol. Chem. 272:12008-13, 1997), DER = Frog Dermaseptin (not used in this study except for design purposes, Mor et al., Biochemistry 30:8824-34, 1991), CER= insect cerotoxin (not used in this study except for design purposes), M-0 = misgurin from loach fish (Park et al., FEBS Letters 411:173-8, 1997). All other peptides are new to this invention. The conserved amino acids are bolded.

MICs

These peptides varied in activity (Table 11), however, the C-terminally capped pleurocidin especially and its N-terminally capped lysine derivative had much better activities against a variety of bacteria including *Vibrio anguillarum* (Va), *Aeromonas salmonicida* (As), *Staphylococcus epidermidis* (C621), *Salmonella typhimurium* wild type (C587) and phoP phoQ mutant (C610), and *Pseudomonas aeruginosa* wild type (K799) and outer membrane barrier altered (Z61). The antimicrobial peptide CEME, a fusion peptide made from portions of an insect defensin ceropin A and the bee venom peptide melittin (Piers and Hancock, *Mol. Microbiol.*, 12:951–8, 1994), as well as the known antibiotics polymyxin B and gentamicin were used as controls. Replacing the pleurocidin N-terminus with the dermaseptin N-terminus had no effect. Replacing pleurocidin N-terminus with the ceratoxin N-terminus reduced activity. Adding lysine to the N-terminus resulted in a slight improvement in antimicrobial activity. Amidating the C-terminus improved antimicrobial activity. Replacing the pleurocidin C-terminus with the misgurin C-terminus had no effect.

TABLE 11

MIC results in Mueller Hinton Broth

| | MIC (µg/ml) | | | | | | | |
|---|---|---|---|---|---|---|---|---|
| Peptide | Va | As | C621 | C587 | C610 | K799 | Z61 | Rank |
| P-0 | 16 | 2 | 64 | 32 | <0.5 | 64 | 16 | 6 |
| P-CN | 2 | 1 | 4 | 4 | <0.5 | 8 | 4 | 2 |
| P-1 | 16 | 2 | 64 | 16 | <0.5 | 32 | 8 | 4 |
| P-1-CN | 2 | 1 | 2 | 2 | <0.5 | 8 | 2 | 1 |
| P-DER | 4 | 1 | 4 | 4 | 0.5 | 16 | 8 | 3 |
| P-CER | 64 | 8 | >64 | >64 | 2 | >64 | >64 | 8 |
| P-M | 32 | 1 | 16 | 16 | 0.5 | 64 | 16 | 5 |
| DER-M | >64 | 2 | 32 | 32 | 0.5 | 64 | 8 | 7 |
| CER-M | >64 | 32 | >64 | >64 | 8 | >64 | 64 | 9 |
| M-0 | >64 | >64 | >64 | >64 | >64 | >64 | >64 | 10 |
| Polymyxin B | 16 | <0.5 | 16 | <0.5 | <0.5 | <0.5 | <0.5 | |
| CEME | 2 | 2 | 4 | 2 | 2 | 4 | 2 | |
| Gentamicin | 1 | <0.5 | 16 | <0.5 | <0.5 | <0.5 | <0.5 | |

Bacteria included *Vibrio anguillarum* (Va), *Aeromonas salmonicida* (As), *Staphylococcus epidermidis* (C621), *Salmonella typhimurium* wild type (C587) and phoP phoQ mutant (C6 10), and *Pseudomonas aeruginosa* wild type (K799) and outer membrane barrier altered (Z61).

P-CN In Vivo Studies in Salmon

Constant delivery of peptide P-CN using intraperitoneal mini-osmotic pumps was carried out. Briefly, juvenile coho salmon were divided into three treatment groups: A. Bacterial injection alone (12 fish). B. Fish saline osmotic pump and bacterial injection (12 fish). C. A combination of P-CN osmotic pump and bacterial injection (19 fish). The fish were anaesthetized and implanted (peritoneal cavity) with mini-osmotic pumps having a pumping rate of 0.13 □l/hour. Heaters were placed in the tanks to keep the water temperature between 12 and 13° C. Pumps were filled with concentrated P-CN to deliver approximately 250 µl/day peptide to fish over a 30-day period. Twelve days after pump implantation, the fish received intraperitoneal injections of *V. anguillarum* (105 bacteria/fish). Mortalities were recorded daily and are shown in Table 12. Mortalities were first noticed on day 3 for the group injected with bacteria alone and on day 5 for the group which received saline osmotic pumps as well as bacterial injections. However, there was no significant difference in mortality between the bacterial injection alone group and the saline osmotic pump group (67% vs. 75%). Mortalities were delayed for the P-CN osmotic pump group. The P-CN osmotic pump group had only one fish die on day 6 over the 30 days experiments with an accumulated mortality of 5%. These results suggested that P-CN was very effective in delaying and reducing mortality in *V. anguillarum* infected fish. Furthermore, since cationic peptides are not effective in a single treatment and constant administration is necessary, this argues for the potential success of transgenic fish expressing peptide P-CN.

TABLE 12

Protection of coho salmon with peptide P-CN administered by osmotic pump

| Time after V. Anguillarum challenge (days) | Mortalities | | |
|---|---|---|---|
| | Bacteria Alone (12 Fish) | Saline Pump Control (12 Fish) | P-CN Treated (19 Fish) |
| 1 | | | |
| 2 | | | |
| 3 | 1 | | |
| 4 | 4 | | |
| 5 | 3 | 4 | |
| 6 | | 2 | 1 |
| 7 | | 2 | |
| 8 | | | |
| 9 | | | |
| 10 | | | |
| 11 | | | |
| Accumulated Mortalities | 67% | 75% | 5% |

EXAMPLE 7

Production of Transgenic Fish

Construct and Vector

Cationic peptide gene expression in transgenic fish will be dependent on the nature of the construct employed and site of integration. The transgenic fish vectors developed by Devlin have different salmonid promoter regions jointed by a polylinker to the terminator region from the type-1 growth hormone gene from sockeye salmon (Devlin et al., *Genetics* 19:372–378, 1994). The metallothionin (MT) promoter has been shown to be active in salmonid tissue-culture cell lines (Chan and Devlin, *Mol. Mar. Biol. Biotech.*, 2:308–318, 1993) to effectively drive the expression of salmon GH genes in transgenic fish and result in dramatically enhanced growth (Devlin et al., *Nature* 371:209–210, 1994). The MT promoter was thus chosen for the antimicrobial peptide transgenic construct. The level of transcription transgenes is dependent not only on the promoter utilized but also on the overall structure of the construct, including the presence of introns, signal peptide and correct polyadenylation. Translation of the processed mRNA into peptide occurs on the ER surface, and secretion out of the cell requires the presence of a leader peptide sequence. The signal peptide gene from salmon GH (GH1-SP) was included because the use of this leader peptide has been shown to elevate GH protein levels in the blood of transgenic animals. Although unknown for fish cells, stabilization of the basic cationic peptides in insect and mammalian cell is mediated by fusion to an acidic propeptide region. After secretion, the pro region is cleaved from the cationic peptide during processing. The propeptide gene in the antimicrobial peptide construct might contribute to stabilization of the cationic peptide. Therefore, the antimicrobial peptide construct contains the MT promoter, signal peptide sequences derived from the type- 1 GH gene, a anionic propeptide region for antimicrobial peptide, a synthetic antimicrobial peptide gene, and the terminator region.

The propeptide region and antimicrobial peptide are fused to the construct containing combination of the promoter, signal peptide, and terminator using standard PCR procedures. Four primers are designed for PCR. Primer □a□ includes several 3□ sequences of GH1-SP and 5□ sequences of the propeptide region. Primer □b□ contains 3□ sequences of the pro region and 5□ sequences of antimicrobial peptide gene. Primer □c□ includes the 3□ end of the pro region and 5□ end of the antimicrobial peptide gene. Primer □d□ is a combination of the 3□ end of the antimicrobial peptide gene and an XbaI site. The complete construct is then cloned into the pBluescript□ II KS plasmid and the construct DNA was thus generated. Prior to gene transfer all the vector sequences were removed by cleavage at NotI sites.

Gene Transfer and Retention

The most common method used to date is microinjection. To transfer DNA into the germ line of salmonids, the antimicrobial peptide constrct is microinjected into the cytoplasm of fertilized eggs in early development. Linear DNA is retained more effectively than the circular DNA in early development (Iyengar et al., *Mol. Mar. Biol. Biotech.*, 4:248–254, 1995). The frequency of germline transformation usually is very low for circular DNA. Therefore, linear DNA, from which all the vector sequences are removed, is utilized. According to the availability of fish eggs, the gene is transferred into cutthrout trout (or coho salmon) eggs using an established microinjection procedure. Briefly, fertilized eggs which have been developmentally arrested and retain soft chorions are microinjected with 2 nL of DNA solution (containing $10^7$ copies of the gene construct) into the perimycropylar region, through the chorion and vitelline membrane into the egg cytoplasm. By this method, DNA is introduced into the vicinity of both the male and female pronuclei, and integration into host chromosomes occurs on average during the first through third cleavage divisions. More than 80 eggs (and up to 1000 eggs) are microinjected. Injected eggs are allowed to develop into fry over approximately 4–6 months. With other constrcts that do not have an effect on viability, a typical survival rate would be approximately 70% at this stage with 1–2% transgenic salmonids.

To identify the transgenic individuals, one year and three month old cutthroat trout transfected with the antimicrobial peptide construct are bled to obtain plasma. The plasma samples are analyzed by PCR using construct-specific oligonucleotide primers. Primer MT-1 is from the MT promoter sequences while primer GH-19 is from the GH signal peptide sequences of the type 1 growth hormone gene. In a typical experiment involving an antimicrobial peptide transgenic construct, of 40 individuals screened three transgenic animals containing the antimicrobial peptide transgene were identified.

Levels of the active peptide secreted from these transgenic fish are monitored by ELISA using polyclonal antibodies against antimicrobial peptide raised in rabbits. Since antimicrobial peptides are small (13–30 amino acids), a carrier protein keyhole limpet hemocyanin (KLH), is coupled to the peptide. Most transgenic trout expressing peptide are reared for subsequent breeding (typically 80% of founder transgenics are germ-line transformed). The remaining fish are subjected to analysis of blood and tissue samples, by ELISA, for evidence of the cationic peptide.

As the period to maturation is long for salmonids and the number of parental transgenic fish is limited, it is not possible to conduct fish challenge studies on these fish. When sufficient numbers of individuals with elevated levels of antimicrobial peptide are obtained (i.e. during the first generation), disease challenge studies are undertaken to evaluate the influence of the antimicrobial peptide on non-specific fish immunity.

SUMMARY

Fish loss from disease is a significant problem in aquaculture worldwide. However, expression of natural cationic peptide genes in fish could increase disease resistance because of continual cellular production of the antimicrobial peptides. In order to choose optimal peptides for transgenic fish, the antimicrobial activities of some cationic peptides were determined by testing minimum inhibitory concentrations (MICs) in vitro. Although several cationic peptides shown to have antimicrobial activities, the most effective cationic peptides tested were CEME, a cecropin/mellitin hybrid peptide, and pleurocidin-CN, a C-terminal amidated form of the flounder fish peptide. The in vivo effect of CEME was examined by intraperitoneal injection of the peptide along with *V. anguillarum* into juvenile coho salmon. Fish in the bacteria alone control group had 60% mortality, while fish receiving peptide and bacteria injections had 82% mortality. Apparently, a single injection of CEME did not protect fish from the bacteria infection. Therefore, constant delivery of CEME and Pleurocidin-CN using intraperitoneal mini-osmotic pumps were carried out. Twelve days after pump implantation, the fish received intraperitoneal injections of *V. anguillarum*. The CEME and pleurocidin-CN pump group had longer survival time and lower mortalities than the control groups (50% Vs. 13%, and 75% Vs. 5%, respectively). Indolicidin transgenic cutthroat trout were made using a construct including an MT promoter, growth hormone signal, pre-region, indolicidin, and terminator. Transgenic individuals were identified by serum analysis using PCR with construct-specific oligonucleotide primers. The development of disease resistant transgenic fish will greatly contribute to the fish aquaculture.

The invention now being fully described, it will be apparent to one of ordinary skill in the art that many changes and modifications can be made thereto without departing from the spirit or scope of the appended claims.

What is claimed is:

1. A method of inhibiting the growth of bacteria or, a virus comprising contacting the bacteria with an inhibiting effective amount of a peptide having an amino acid sequence selected from the group consisting of:

| | |
|---|---|
| KWKSFIKKLTSAAKKVVTTAKPLALIS; | (SEQ ID NO:3) |
| KWKSFIKKLTKAAKKVVTTAKKPLIV; | (SEQ ID NO:4) |
| KWKKFIKSLTKSAAKTVVKTAKKPLIV; | (SEQ ID NO:5) |
| KWKLFKKIGIGAVLKVLKVLTTGLPALKLTLK; | (SEQ ID NO:6) |
| KLFKKIGIGAVLKVLKVLTTGLPALKLTLK; | (SEQ ID NO:7) |
| KWKFKKIGIGAVLKVLKVLTTGLPALKLTLK; | (SEQ ID NO:8) |
| KLWKLFKKIGIGAVLKVLKVLTTGLPALKLTLK; | (SEQ ID NO:9) |
| KWKSFIKKLTSAAKKVVTTAAKPLTK; | (SEQ ID NO:10) |
| KWKKFIKKIGIGAVLKVLTTGLPALKLTKK; | (SEQ ID NO:11) |
| KKWKKFIKKIGIGAVLTTPGAKK; | (SEQ ID NO:12) |
| GWGSFFKKAAHVGKHVGKAALTHYL-NH2; | (SEQ ID NO:14) |
| KGWGSFFKKAAHVGKHVGKAALTHYL; | (SEQ ID NO:15) |
| KGWGSFFKKAAHVGKHVGKAALTHYL-NH2; | (SEQ ID NO:16) |
| ALWKTMLKKAAHVGKHVGKAALTHYL-NH2; | (SEQ ID NO:17) |
| SIGSAFKKAAHVGKHVGKAALTHYL-NH2; | (SEQ ID NO:18) |
| GWGSFFKKAAHVGKHVGKAALGAAARRRK; | (SEQ ID NO:19) |
| ALWKTMLKKAAHVGKHVGKAALGAAARRRK; and | (SEQ ID NO:20) |
| SIGSAFKKAAHVGKHVGKAALGAAARRRK; | (SEQ ID NO:21) | and amidated variations and conservative variations thereof.

2. The method of claim 1, wherein the bacteria is gram positive.

3. The method of claim 2, wherein the bacteria is selected from the group consisting of *Staphylococcus typhimurium, Staphylococcus aureus, Listeria monocytogenes, Corynebacterium xerosis, Streptococcus pyogenes, Streptococcus pneumoniae, Streptococcus mitis* and *Staphylococcuus epidermidis*.

4. The method of claim 1, wherein the bacteria is gram negative.

5. The method of claim 4, wherein the bacteria is selected from the group consisting of *Escherichia coli, Pseudomonas aeruginosa, Enterobacter facaelis, Salmonella typhimurium, Salmonella typhimurium phoP phoQ, Aeromonas salmonicida, Vibrio anguillarum* and *Enterobacter cloacae.*

6. The method of claim 1, wherein the contacting comprises a peptide in combination with at least one antibiotic or with lysozyme.

7. The method of claim 6, wherein the antibiotic is selected from the group consisting of aminoglycosides, penicillins, cephalosporins, carbapenems, monobactams, quinolones, tetracyclines, and glycopeptides.

8. The method of claim 7, wherein the antibiotic is selected from the group consisting of amikacin, gentamicin, kanamycin, netilmicin, tobramycin, streptomycin, azithromycin, clarithromycin, erythromycin, erythromycin estolate/ethyl-succinate/gluceptate/lactobionate/stearate, penicillin G, penicillin V, methicillin, nafcillin, oxacillin, cloxacillin, dicloxacillin, ampicillin, amoxicillin, ticarcillin, carbenicillin, mezlocillin, azlocillin, piperacillin, cephalothin, cefazolin, cefaclor, c-efamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, cefsulodin, imipenem, aztreonam, fleroxacin, nalidixic acid, norfloxacin, ciprofloxacin, ofloxacin, enoxacin, lomefloxacin, cinoxacin, doxycycline, minocycline, tetracycline, vancomycin, chloramphenicol, clindamycin, trimethoprim, sulfamethoxazole, nitrofurantoin, rifampin and mupirocin and teicoplanin.

9. A method of inhibiting an endotoxemia or sepsis associated disorder in a subject having or at risk of having such a disorder, comprising administering to the subject a therapeutically effective amount of a peptide having an amino acid sequence selected from the group consisting of:

| | |
|---|---|
| KWKSFIKKLTSAAKKVVTTAKPLALIS; | (SEQ ID NO:3) |
| KWKSFIKKLTKAAKKVVTTAKKPLIV; | (SEQ ID NO:4) |
| KWKKFIKSLTKSAAKTVVKTAKPLIV; | (SEQ ID NO:5) |
| KWKLFKK1GIGAVLKVLKVLTTGLPALKLTLK; | (SEQ ID NO:6) |
| KLFKKIGIGAVLKVLKVLTTGLPALKLTLK; | (SEQ ID NO:7) |
| KWKFKKIGIGAVLKVLKVLTTGLPALKLTLK; | (SEQ ID NO:8) |
| KLWKLFKKIGIGAVLKVLKVLTTGLPALKLTLK; | (SEQ ID NO:9) |
| KWKSFIKKLTSAAKKVTTAAKPLTK; | (SEQ ID NO:10) |
| KWKKFIKKIGIGAVLKVLTTGLPALKLTKK; and | (SEQ ID NO:11) |
| KKWKKFIKKIGIGAVLTTPGAKK; | (SEQ ID NO:12) | and amidated variations and conservative variations thereof.

10. The method of claim 9, wherein the disorder is septic shock.

11. The method of claim 9, wherein the peptide is administered in combination with at least one antibiotic or with lysozyme.

12. The method of claim 11, wherein the antibiotic is selected from the group consisting of aminoglycosides, penicillins, cephalosporins, carbapenems, monobactams, quinolones, tetracyclines, and glycopeptides.

13. The method of claim 12, wherein the antibiotic is selected from the group consisting of amikacin, gentamicin, kanamycin, netilmicin, tobramycin, streptomycin, azithromycin, clarithromycin, erythromycin, erythromycin estolate-/ethylsuccinate/gluceptate/lactobionate/stearate, penicillin G, penicillin V, methicillin, nafcillin, oxacillin, cloxacillin, dicloxacillin, ampicillin, amoxicillin, ticarcillin, carbenicillin, mezlocillin, azlocillin, piperacillin, cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, cefsulodin, imipenem, aztreonam, fleroxacin, nalidixic acid, norfloxacin, ciprofloxacin, ofloxacin, enoxacin, lomefloxacin, cinoxacin, doxycycline, minocycline, tetracycline, vancomycin, chloramphenicol, clindamycin, trimethoprim, sulfamethoxazole, nitrofurantoin, rifampin, mupirocin and teicoplanin.

14. A method of inhibiting the growth of a eukaryotic cell comprising contacting the eukaryotic cell with an inhibiting effective amount of a peptide having an amino acid sequence selected from the group consisting of:

| | |
|---|---|
| KWKLFKKIGIGAVLKVLTTGLPALKLTK; | (SEQ ID NO:1) |
| KWKSFIKKLTTAVKKVLTTGLPALIS; | (SEQ ID NO:2) |
| KWKSFIKKLTSAAKKVVTTAKPLALIS; | (SEQ ID NO:3) |
| KWKSFIKKLTKAAKKVVTTAKKPLIV; | (SEQ ID NO:4) |
| KWKKFIKSLTKSAAKTVVKTAKKPLIV; | (SEQ ID NO:5) |
| KWKLFKKIGIGAVLKVLKVLTTGLPALKLTLK; | (SEQ ID NO:6) |
| KLFKKIGIGAVLKVLKVLTTGLPALKLTLK; | (SEQ ID NO:7) |
| KWKFKKIGIGAVLKVLKVLTTGLPALKLTLK; | (SEQ ID NO:8) |
| KLWKLFKKIGIGAVLKVLKVLTTGLPALKITLK; | (SEQ ID NO:9) |
| KWKSFIKKLTSAAKKVTTAAIKPLTK; | (SEQ ID NO:10) |
| KWKKFIKKIGIGAVLKVLTTGLPALKLTKK; | (SEQ ID NO:11) |
| KKWKKFIKKIGIGAVLTTPGAKK; | (SEQ ID NO:12) |
| GWGSFFKKAAHVGKHVGKAALTHYL; | (SEQ ID NO:13) |
| GWGSFFKKAAHVGKHVGKAALTHYL-NH2; | (SEQ ID NO:14) |
| KGWGSFFKLKAAHVGKHVGKAALTHYL; | (SEQ ID NO:15) |
| KGWGSFFKKAAHVGKHVGKAALTHYL-NH2; | (SEQ ID NO:16) |
| ALWKTMLKKAAHVGKHVGKAALTHYL-NH2; | (SEQ ID NO:17) |
| SIGSAFKKAAHVGKHVGKAALTHYL-NH2; | (SEQ ID NO:18) |
| GWGSFFKKAAHVGKHVGKAALGAAARRRK; | (SEQ ID NO:19) |
| ALWKTMLKKAAHVGKHVGKAALGAAARRRK; | (SEQ ID NO:20) |
| SIGSAFKKAAHVGKHVGKAALGAAARRRK; | (SEQ ID NO:21) |
| RQRVEELSKFSKKGAAARRRK; | (SEQ ID NO:22) |
| ALWKTMLKKLGTMALHAGKAALGAAADTISQTQ; and | (SEQ ID NO:23) |
| SIGSAFKKALPVAKKIGKAALPIAKAALP; | (SEQ ID NO:24) | and amidated variations and conservative variations thereof.

15. The method of claim 14, wherein the eukaryotic cell is an animal cell.

16. The method of claim 14, wherein the eukaryotic cell is a neoplastic cell.

17. The method of claim 16, wherein the neoplastic cell is a glioblastoma cell.

18. The method of claim 14, wherein the peptide is administered in combination with at least one chemotherapeutic agent.

19. The method of claim 18, wherein the chemotherapeutic agent is selected from the group consisting of bleomycin, neocarsinostatin, suramin, doxorubicin, taxol, mitomycin C and cisplatin.

20. A method of inhibiting the growth of bacteria comprising contacting the bacteria with an inhibiting effective amount of a peptide having an amino acid sequence selected from the group consisting of:

```
GWGSFFKKAAHVGKHVGKAALTHYL-NH2;   (SEQ ID NO:14)
KGWGSFFKKAAHVGKHVGKAALTHYL;      (SEQ ID NO:15)
KGWGSFFKKAAHVGKHVGKAALTHYL-NH2;  (SEQ ID NO:16)
ALWKTMLKKAAHVGKHVGKAALTHYL-NH2;  (SEQ ID NO:17)
SIGSAFKKAAHVGKHVGKAALTHYL-NH2;   (SEQ ID NO:18)
GWGSFFKKAAHVGKHVGKAALGAAARRRK;   (SEQ ID NO:19)
ALWKTMLKKAAHVGKHVGKAALGAAARRRK;  (SEQ ID NO:20)
SIGSAFKKAAHVGKHVGKAALGAAARRRK;   (SEQ ID NO:21)
``` and amidated variations and conservative variations thereof.

21. A method of inhibiting the growth of bacteria comprising contacting the bacteria with an inhibiting effective amount of a peptide having an amino acid sequence selected from the group consisting of:

```
GWGSFFKKAAHVGKHVGKAALTHYL-NH2;   (SEQ ID NO:14)
KGWGSFFKKAAHVGKHVGKAALTHYL;      (SEQ ID NO:15)
KGWGSFFKKAAHVGKHVGKAALTHYL-NH2;  (SEQ ID NO:16)
ALWKTMLKKAAHVGKHVGKAALTHYL-NH2;  (SEQ ID NO:17)
SIGSAFKKAAHVGKHVGKAALTHYL-NH2;   (SEQ ID NO:18)
GWGSFFKKAAHVGKHVGKAALGAAARRRK;   (SEQ ID NO:19)
ALWKTMLKKAAHVGKHVGKAALGAAARRRK;  (SEQ ID NO:20)
SIGSAFKKAAHVGKHVGKAALGAAARRRK;   (SEQ ID NO:21)
``` and amidated variations and conservative variations thereof.

* * * * *